United States Patent
Maeda et al.

(10) Patent No.: US 9,012,773 B2
(45) Date of Patent: Apr. 21, 2015

(54) THIAZOLE-BASED COMPOUND AND USES THEREOF

(75) Inventors: Katsumi Maeda, Tokyo (JP); Shin Nakamura, Tokyo (JP); Kentaro Nakahara, Tokyo (JP); Terumasa Shimoyama, Tokyo (JP)

(73) Assignee: NEC Corporation, Tokyo (JP)

( * ) Notice: Subject to any disclaimer, the term of this patent is extended or adjusted under 35 U.S.C. 154(b) by 43 days.

(21) Appl. No.: 13/985,248

(22) PCT Filed: Feb. 13, 2012

(86) PCT No.: PCT/JP2012/053269
§ 371 (c)(1),
(2), (4) Date: Aug. 13, 2013

(87) PCT Pub. No.: WO2012/111610
PCT Pub. Date: Aug. 23, 2012

(65) Prior Publication Data
US 2013/0319530 A1  Dec. 5, 2013

(30) Foreign Application Priority Data
Feb. 14, 2011 (JP) ................. 2011-029218

(51) Int. Cl.
*H01L 51/46* (2006.01)
*H01G 9/20* (2006.01)
(Continued)

(52) U.S. Cl.
CPC .......... *H01G 9/2059* (2013.01); *C09B 23/0008* (2013.01); *C09B 23/005* (2013.01);
(Continued)

(58) Field of Classification Search
USPC ....................................... 136/263; 252/501.1
See application file for complete search history.

(56) References Cited

U.S. PATENT DOCUMENTS

2010/0140559 A1   6/2010   Klaus et al.

FOREIGN PATENT DOCUMENTS

JP        2664194 B2    10/1997
JP     2009-187821 A     8/2009
(Continued)

OTHER PUBLICATIONS

Dinesh G. Patel, et al., "Modification of nonlinear optical dyes for dye sensitized solar cells: a new use for a familiar acceptor", Journal of Materials Chemistry, 2011, pp. 4242-4250, vol. 21, No. 12.
(Continued)

*Primary Examiner* — Jayne Mershon
(74) *Attorney, Agent, or Firm* — Sughrue Mion, PLLC

(57) ABSTRACT

The present invention provides a compound useful as a photoelectric conversion dye having excellent photoelectric conversion performance. The compound according to the present invention is a thiazole-based compound represented by the following general formula (1), a tautomer or stereoisomer thereof, or a salt thereof. In the general formula (1), $R^1$ represents a hydrogen atom, a substituted or unsubstituted, linear or branched alkyl group, or a substituted or unsubstituted aryl group, $R^2$ represents a hydrogen atom, a substituted or unsubstituted, linear or branched alkyl group, or a cyano group, D represents an organic group comprising an electron-donating substituent, Z represents a linking group having a heteroaromatic ring or at least one hydrocarbon group selected from the group consisting of an aromatic ring, a vinylene group (—CH═CH—), or an ethynylene group (—C≡C—), and M represents a hydrogen atom or a salt-forming cation.

(1)

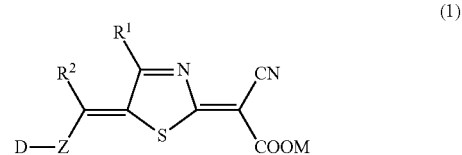

19 Claims, 3 Drawing Sheets

(51) Int. Cl.
- C09B 23/01 (2006.01)
- C09B 23/14 (2006.01)
- C07D 417/14 (2006.01)
- H01L 51/00 (2006.01)

(52) U.S. Cl.
CPC ......... C09B23/0058 (2013.01); C09B 23/0066 (2013.01); C09B 23/14 (2013.01); H01G 9/2031 (2013.01); H01L 51/0061 (2013.01); H01L 51/0068 (2013.01); H01L 51/0069 (2013.01); H01L 51/0072 (2013.01); C07D 417/14 (2013.01); Y02E 10/542 (2013.01)

(56) References Cited

FOREIGN PATENT DOCUMENTS

| JP | 2010-235908 A | 10/2010 |
| JP | 2010-533368 A | 10/2010 |
| JP | 2011-026376 A | 2/2011 |

OTHER PUBLICATIONS

Brian O'Regan, et al., "A low-cost, high-efficiency solar cell based on dye-sensitized colloidal $TiO_2$ Film", Nature, Oct. 24, 1991, pp. 737-740, vol. 353.

THIAZOLE-BASED COMPOUND AND USES THEREOF

CROSS REFERENCE TO RELATED APPLICATIONS

This is a National Stage of International Application No. PCT/JP2012/053269, filed Feb. 13, 2012, claiming priority from Japanese Patent Application No. 2011-029218, filed Feb. 14, 2011, the contents of all of which are incorporated herein by reference in their entirety.

TECHNICAL FIELD

The present invention relates to a thiazole-based compound and uses thereof.

BACKGROUND ART

Global warming has become a serious problem because of an increase in $CO_2$ concentration, which is due to the use of large amounts of fossil fuels, typified by petroleum, so far, and further, the depletion of fossil fuels has been feared. Therefore, how to meet the demand for a large amount of energy in the future has become a very important problem on a global scale. In such circumstances, using light energy, which is infinite and is clean against nuclear power generation, for power generation has been positively studied. As solar cells that convert solar energy into electric energy, inorganic solar cells using inorganic materials, such as single-crystal silicon, polycrystalline silicon, and amorphous silicon, and organic solar cells using organic dyes and conductive polymer materials have been proposed.

In such circumstances, a dye-sensitized solar cell (Gratzel type solar cell) (for example, see Patent Document 1 and Non Patent Document 1) proposed by Dr. Gratzel et al., Switzerland in 1991, has been expected as a next-generation solar cell because, in addition to a simple production process, the same level of conversion efficiency as amorphous silicon is obtained. The Gratzel type solar cell comprises a semiconductor electrode in which a semiconductor layer on which a dye is adsorbed is formed on a conductive basal material, a counter electrode composed of a conductive basal material opposed to the semiconductor electrode, and an electrolyte layer held between the two electrodes.

In the Gratzel type solar cell, the adsorbed dye absorbs light and is in an excited state, and electrons are injected into the semiconductor layer from the excited dye. The dye that is in an oxidized state by the emission of electrons is reduced by the transfer of electrons to the dye due to the oxidation reaction of the redox agent in the electrolyte layer, and returns to the original dye. The redox agent that has donated electrons to the dye is reduced again on the counter electrode side. The Gratzel type solar cell functions as a solar cell that converts light energy into electric energy by this series of reactions.

In the Gratzel type solar cell, by using for the semiconductor layer porous titanium oxide obtained by sintering fine particles, the surface area where the dye is adsorbed, that is, the effective reaction surface area, increases as much as about 1000 times. Compared with a case where a titanium oxide film fabricated by a vapor phase growth method is used, a great feature of the case where porous titanium oxide is used is that larger photocurrent is obtained.

In the Gratzel type solar cells, metal complexes, such as ruthenium complexes, are used as the sensitizing dye, and specifically, for example, a cis-bis(isothiocyanato)-bis-(2,2'-bipyridyl-4,4'-dicarboxylic acid)ruthenium(II) ditetrabutylammonium complex, bipyridine complexes of ruthenium, such as cis-bis(isothiocyanato)-bis-(2,2'-bipyridyl-4,4'-dicarboxylic acid)ruthenium(II), and a tris(isothiocyanato)(2,2':6',2''-terpyridyl-4,4',4''-tricarboxylic acid)ruthenium(II) tritetrabutylammonium complex, which is one of terpyridine complexes of ruthenium, are used.

PRIOR ART DOCUMENT

Patent Document

Patent Document 1: JP 2664194 B2

Non Patent Document

Non Patent Document 1: Nature 353 (1991) 737-740.

DISCLOSURE OF INVENTION

Problem to be Solved by the Invention

As described above, in the dye-sensitized solar cells described in Background Art, metal complexes comprising precious metals, such as ruthenium complexes are used as the sensitizing dye. For example, when a dye-sensitized solar cell using a ruthenium complex is mass-produced, a problem may occur in respect of "restriction in terms of resources" because ruthenium has many uses, such as catalysts. In addition, since a precious metal is used, the dye-sensitized solar cell is expensive, which also prevents its spread. Therefore, the development of an organic dye not comprising a precious metal, such as ruthenium, as a sensitizing dye used in a dye-sensitized solar cell, is required. Generally, an organic dye has a larger molar absorption coefficient and further greater flexibility in molecular design than a metal complex, such as ruthenium complexes, and therefore, the development of an organic dye with high photoelectric conversion efficiency is expected.

The present invention has been made in order to solve the above problems, and it is an object of the present invention to provide a thiazole-based compound that has excellent photoelectric conversion performance and may be used for a dye for photoelectric conversion or the like, a dye for photoelectric conversion having excellent photoelectric conversion performance which comprises the thiazole-based compound, a semiconductor electrode for a photoelectrochemical cell, a photoelectric conversion device for a photoelectrochemical cell, and a photoelectrochemical cell in which the dye is used.

Means for Solving the Problems

The thiazole-based compound according to the present invention is
a thiazole-based compound represented by the following general formula (1), a tautomer or stereoisomer thereof, or a salt thereof,

[Chemical formula 1]

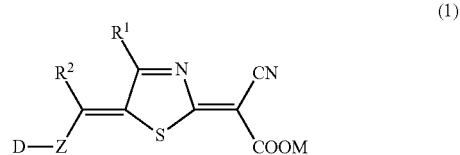

wherein

R¹ represents a hydrogen atom, a substituted or unsubstituted, linear or branched alkyl group, or a substituted or unsubstituted aryl group, R² represents a hydrogen atom, a substituted or unsubstituted, linear or branched alkyl group, or a cyano group, D represents an organic group comprising an electron-donating substituent, Z represents a linking group having a heteroaromatic ring or at least one hydrocarbon group selected from the group consisting of an aromatic ring, a vinylene group (—CH=CH—), or an ethynylene group (—C≡C—), and M represents a hydrogen atom or a salt-forming cation.

The dye for photoelectric conversion of the present invention comprises at least one of the thiazole-based compound represented by the general formula (1), a tautomer or stereoisomer thereof, or a salt thereof according to the present invention.

A semiconductor electrode for a photoelectrochemical cell according to the present invention comprises a semiconductor layer comprising the dye for photoelectric conversion according to the present invention.

A photoelectric conversion device for a photoelectrochemical cell according to the present invention comprises the semiconductor electrode for a photoelectrochemical cell according to the present invention.

In addition, the photoelectrochemical cell according to the present invention comprises the photoelectric conversion device for a photoelectrochemical cell according to the present invention.

Effect of Invention

The present invention may provide a thiazole-based compound that may be used for a dye for photoelectric conversion or the like and has excellent photoelectric conversion performance, a dye for photoelectric conversion having excellent photoelectric conversion performance which comprises the thiazole-based compound, a semiconductor electrode for a photoelectrochemical cell, a photoelectric conversion device for a photoelectrochemical cell, and a photoelectrochemical cell in which the dye is used.

DESCRIPTION OF SYMBOLS

Figure 1:
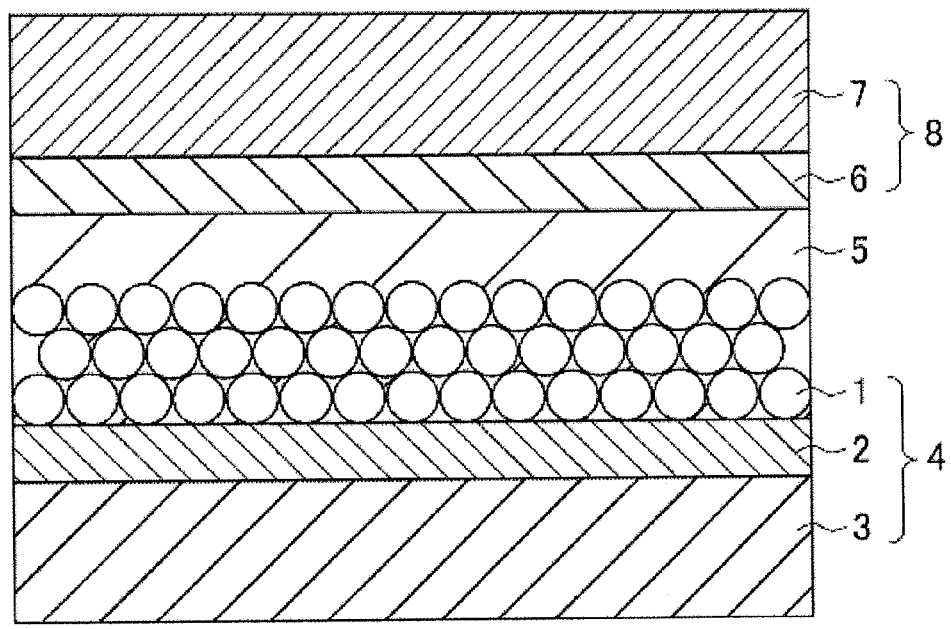
FIG. 1 is a cross-sectional view schematically showing the structure of one example of a photoelectric conversion device for a photoelectrochemical cell according to the present invention.

The numeral symbols given in FIG. 1 mean the following.
1 a semiconductor layer
2 a transparent conductive layer
3 a light-transmitting substrate
4 a semiconductor electrode for a photoelectrochemical cell
5 an electrolyte layer (charge transporting layer)
6 a catalyst layer
7 a substrate
8 a counter electrode

BEST MODE FOR CARRYING OUT THE INVENTION

The present invention will be explained in detail below by referring to examples thereof.

<Thiazole-Based Compound>

The thiazole-based compound according to the present invention is a thiazole-based compound represented by the following general formula (1), a tautomer or stereoisomer thereof, or a salt thereof, as described above.

[Chemical formula 2]

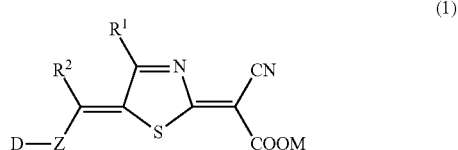

(1)

wherein

R¹ represents a hydrogen atom, a substituted or unsubstituted, linear or branched alkyl group, or a substituted or unsubstituted aryl group, R² represents a hydrogen atom, a substituted or unsubstituted, linear or branched alkyl group, or a cyano group, D represents an organic group comprising an electron-donating substituent, Z represents a linking group having a heteroaromatic ring or at least one hydrocarbon group selected from the group consisting of an aromatic ring, a vinylene group (—CH=CH—), or an ethynylene group (—C≡C—), and M represents a hydrogen atom or a salt-forming cation.

When isomers, such as tautomers or stereoisomers (examples: geometrical isomers, conformational isomers, and optical isomers), are present for the thiazole-based compound of the present invention, any isomer may be used in the present invention. In addition, the salt of the thiazole-based compound of the present invention may be an addition salt with an acid, but may be an addition salt with a base. Further, the acid for forming the addition salt with an acid may be an inorganic acid or an organic acid, and the base for forming the addition salt with a base may be an inorganic base or an organic base. The inorganic acid is not particularly limited, and examples thereof include sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluoric acid, chloric acid, bromic acid, iodic acid, perfluoric acid, perchloric acid, perbromic acid, and periodic acid. The organic acid is also not particularly limited, and examples thereof include p-toluenesulfonic acid, methanesulfonic acid, oxalic acid, p-bromobenzenesulfonic acid, succinic acid, citric acid, benzoic acid, and acetic acid. The inorganic base is not particularly limited, and examples thereof include ammonium hydroxide, alkali metal hydroxides, alkaline-earth metal hydroxides, carbonates, and hydrogen carbonates, more specifically sodium hydroxide, potassium hydroxide, potassium carbonate, sodium carbonate, sodium hydrogen carbonate, potassium hydrogen carbonate, calcium hydroxide, and calcium carbonate. The organic base is also not particularly limited, and examples thereof include alcohol amines, trialkylamines, tetraalkylammoniums, and tris(hydroxymethyl)aminomethane.

Examples of the alcohol amines include ethanolamine. Examples of the trialkylamines include trimethylamine, triethylamine, tripropylamine, tributylamine, and trioctylamine. Examples of the tetraalkylammoniums include tetramethylammonium, tetraethylammonium, tetrapropylammonium, tetrabutylammonium, and tetraoctylammonium. The method for producing those addition salts is also not particularly limited, and, for example, those addition salts may be produced by a method of appropriately adding the acids or bases as described above to the thiazole-based compound by using a conventional technique, or the like.

In the present invention, the number of carbon atoms of an alkyl group is selected, for example, from 1 to 12, preferably from 1 to 8, and the number of carbon atoms of an aryl group is selected, for example, from 5 to 24, preferably from 6 to 12. In the case of a substituted alkyl group or a substituted aryl group, the number of carbon atoms described above does not include the number of carbon atoms of a substituent. In the present invention, specific examples of an alkyl group include a methyl group, an ethyl group, a n-propyl group, an isopropyl group, a n-butyl group, an isobutyl group, a sec-butyl group, a tert-butyl group, a pentyl group, a hexyl group, a heptyl group, an octyl group, a nonyl group, a decyl group, an undecyl group, and a dodecyl group. The same applies to a group comprising an alkyl group in the structure (an alkylamino group, an alkoxy group, an alkanoyl group, and the like). In the present invention, a substituted alkyl group may be a substituted alkyl group in which the alkyl group (unsubstituted alkyl group) is substituted by any substituent. The number of substituents of the substituted alkyl group may be one or plural. When the number of substituents is plural, the substituents may be the same or different. Examples of the substituent of the substituted alkyl group include a hydroxy group, alkoxy groups, and aryl groups (for example, a phenyl group). Specific examples of the substituted alkyl group include aralkyl groups, such as a benzyl group.

In the present invention, an aryl group includes a heteroaryl group unless particularly limited. Specific examples thereof include a phenyl group, a biphenyl group, a naphthyl group, an anthryl group, a phenanthryl group, a pyrenyl group, a pyridyl group, a quinolyl group, an acridyl group, a pyrrolyl group (1H-pyrrolyl group), a furanyl group (furyl group), a thienyl group, a carbazoyl group, and a fluorenyl group. In the present invention, a substituted aryl group may be a substituted aryl group in which the aryl group (unsubstituted aryl group) is substituted by any substituent. The number of substituents of the substituted aryl group may be one or plural. When the number of substituents is plural, the substituents may be the same or different. Examples of the substituent of the substituted aryl group include alkyl groups, a hydroxy group, alkoxy groups, an amino group, alkylamino groups, and dialkylamino groups. In the present invention, specific examples of a substituted or unsubstituted aryl group include a phenyl group, a biphenyl group, a tolyl group, a 4-tert-butylphenyl group, a 4-methoxyphenyl group, a 4-cyanophenyl group, a 4-hydroxyphenyl group, and a 4-chlorophenyl group.

Generally, an aryl group means a monovalent group (Ar—) derived from an "aromatic hydrocarbon (ArH)," and "aromatic hydrocarbons (ArH)" include benzenoid aromatic hydrocarbons and non-benzenoid aromatic hydrocarbons. In the present invention, as an "aryl group," an aryl group derived from a benzenoid aromatic hydrocarbon is preferably used.

In the present invention, an alkenyl group may be a structure in which any carbon-carbon bond of an alkyl group is converted into a double bond by dehydrogenation. In the present invention, an acyl group is not particularly limited, and examples thereof include a formyl group, an acetyl group, a propionyl group, an isobutyryl group, a valeryl group, an isovaleryl group, a pivaloyl group, a hexanoyl group, a cyclohexanecarbonyl group, a benzoyl group, and an ethoxycarbonyl group ($C_2H_5$—O—CO—). The same applies to a group comprising an acyl group in the structure (an acyloxy group, an alkanoyloxy group, and the like). In the present invention, the number of carbon atoms of an acyl group includes the number of carbonyl carbon atoms, and, for example, an alkanoyl group (acyl group) having 1 carbon atom refers to a formyl group. In the present invention, a "halogen" refers to any halogen element, and examples thereof include fluorine, chlorine, bromine, and iodine.

In the present invention, acyclic groups, such as an alkyl group, an alkoxy group, an alkenyl group, and an alkanoyl group, may be linear or branched unless particularly limited. In the present invention, when isomers are present for a substituent or the like, any isomer may be used unless particularly limited. For example, a simple term "propyl group" may be either of a n-propyl group and an isopropyl group. A simple term "butyl group" may be any one of a n-butyl group, an isobutyl group, a sec-butyl group, and a tert-butyl group. A simple term "naphthyl group" may be any one of a 1-naphthyl group and a 2-naphthyl group.

D in the general formula (1) represents an organic group comprising an electron-donating substituent, as described above. The organic group D comprising an electron-donating substituent is preferably a moiety represented by the following general formula (2) or general formula (3):

[Chemical formula 3]

(2)

[Chemical formula 4]

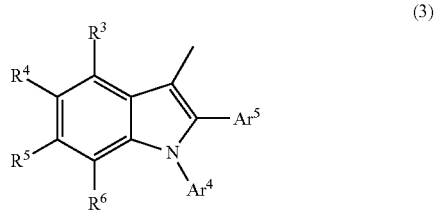
(3)

In the general formula (2), $Ar^1$ and $Ar^2$ each independently represent a substituted or unsubstituted alkyl group, or a substituted or unsubstituted aryl group or heterocyclic group. As the substituted or unsubstituted heterocyclic group used for $Ar^1$ and $Ar^2$, a substituted or unsubstituted heteroaromatic ring group may be preferably used. In the general formula (3), $Ar^4$ and $Ar^5$ each independently represent a substituted or unsubstituted alkyl group, or a substituted or unsubstituted aryl group or heteroaromatic ring group. Examples of the substituted or unsubstituted alkyl group include alkyl groups having 1 to 8 carbon atoms, such as a methyl group, an ethyl group, a propyl group, a n-butyl group, a pentyl group, a hexyl group, a heptyl group, and an octyl group, and aralkyl groups, such as a benzyl group. Examples of the substituent bonded to the alkyl group include a hydroxy group, alkoxy groups (for example, alkoxy groups having 1 to 4 carbon atoms), and a phenyl group. Examples of the substituted or unsubstituted aryl group include substituted or unsubstituted aryl groups having 6 to 22 carbon atoms, such as a phenyl group, a tolyl group, a 4-t-butylphenyl group, a 3,5-di-t-butylphenyl group, a 4-methoxyphenyl group, a 4-hexyloxyphenyl group, a 4-octyloxyphenyl group, a 4-(N,N-dimethylamino)phenyl group, a 4-(N,N-dioctylamino)phenyl group, and a 4-(N,N-diphenylamino)phenyl group. Examples of the substituent bonded to the aryl group include alkyl groups (for example, alkyl groups having 1 to 8 carbon atoms), a hydroxy group, alkoxy groups (for example, alkoxy groups having 1 to 8 carbon atoms), N,N-dialkylamino groups (the alkyl group used therein is, for example, an alkyl group having 1 to 8 carbon atoms), and a N,N-diphenylamino group. Examples of the substituted or unsubstituted heteroaromatic ring group include a thienyl group, a furyl group, a pyrrolyl group (1H-pyrrolyl group), an indolyl group, and a carbazoyl group. Examples of the substituent bonded to the heteroaromatic ring group include alkyl groups (for example, alkyl groups having 1 to 8 carbon atoms), a hydroxy group, and alkoxy groups (for example, alkoxy groups having 1 to 8 carbon atoms). $Ar^3$ represents a substituted or unsubstituted arylene group, or a substituted or unsubstituted divalent heterocyclic group. As the substituted or unsubstituted divalent heterocyclic group used for $Ar^3$, a substituted or unsubstituted divalent heteroaromatic ring group may be preferably used. Examples of the substituted or unsubstituted arylene group include a phenylene group and a naphthylene group. Examples of the substituent bonded to the arylene group include alkyl groups (for example, alkyl groups having 1 to 8 carbon atoms), a hydroxy group, and alkoxy groups (for example, alkoxy groups having 1 to 8 carbon atoms). Examples of the substituted or unsubstituted divalent heteroaromatic ring group include a thiophenediyl group, a furandiyl group, and a pyrrolediyl group (for example, a 1H-pyrrolediyl group). Examples of the substituent bonded to the divalent heteroaromatic ring group include alkyl groups (for example, alkyl groups having 1 to 8 carbon atoms), a hydroxy group, and alkoxy groups (for example, alkoxy groups having 1 to 8 carbon atoms). For example, regarding a thiophenediyl group, a furandiyl group, and a pyrrolediyl group (for example, a 1H-pyrrolediyl group), those having a -2,5-diyl structure are preferably selected. Regarding a phenylene group, one having a -1,4-diyl structure is preferably selected.

Generally, an arylene group means a divalent group (—Ar—) derived from an "aromatic hydrocarbon (HArH)," and having bonds on different carbon atoms that compose its aromatic ring, and "aromatic hydrocarbons (HArH)" include benzenoid aromatic hydrocarbons and non-benzenoid aromatic hydrocarbons. In the present invention, as the "arylene group," an arylene group derived from a benzenoid aromatic hydrocarbon is preferably used.

In the general formula (3), $R^3$ to $R^6$ each independently represent a hydrogen atom, a substituted or unsubstituted, linear or branched alkyl group, a substituted or unsubstituted aryl group, an alkoxy group, a hydroxyl group, or a N,N-dialkylamino group. Examples of the substituted or unsubstituted, linear or branched alkyl group include a methyl group, an ethyl group, a propyl group, a n-butyl group, a isobutyl group, a sec-butyl group, a tert-butyl group, a pentyl group, a hexyl group, a heptyl group, and an octyl group. Examples of the substituted or unsubstituted aryl group include a phenyl group, a tolyl group, a 4-t-butylphenyl group, a 4-methoxyphenyl group, and a 4-(N,N-dimethylamino)phenyl group. Examples of the alkoxy group include a methoxy group, an ethoxy group, a propoxy group, and a butoxy group. Examples of the N,N-dialkylamino group include a N,N-dimethylamino group and a N,N-diethylamino group.

Specific examples of the organic group D comprising an electron-donating substituent other than the moiety represented by the general formula (2) or general formula (3) are shown in the following chemical formulae (D1) to (D13), but are not limited to those. R in the following chemical formulae (D3) to (D6) and (D9) to (D13) represents a substituted or unsubstituted alkyl group, or a substituted or unsubstituted aryl group. Examples of the substituted or unsubstituted alkyl group include alkyl groups having 1 to 8 carbon atoms, such as a methyl group, an ethyl group, a propyl group, a n-butyl group, an isobutyl group, a sec-butyl group, a tert-butyl group, a pentyl group, a hexyl group, a heptyl group, and an octyl group. Examples of the substituted or unsubstituted aryl group include a phenyl group, a tolyl group, a 4-t-butylphenyl group, a 3,5-di-t-butylphenyl group, a 4-methoxyphenyl group, and a 4-(N,N-dimethylamino) phenyl group.

[Chemical formula 5]

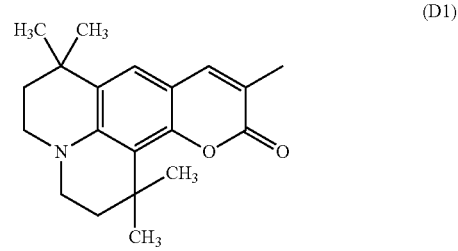

(D1)

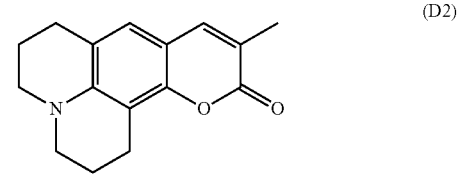

(D2)

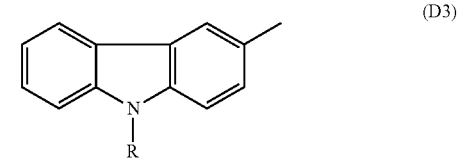

(D3)

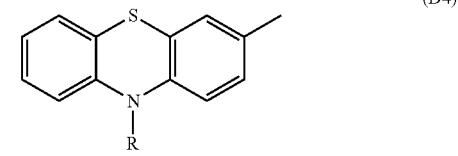

(D4)

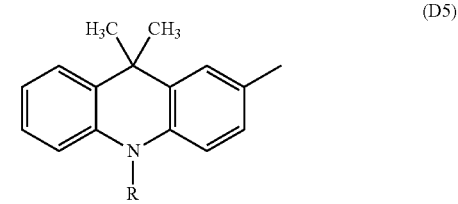

(D5)

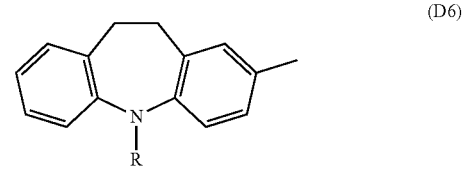

(D6)

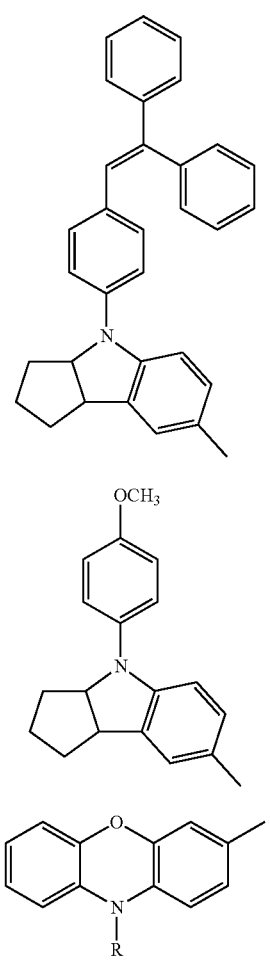

[Chemical formula 6]

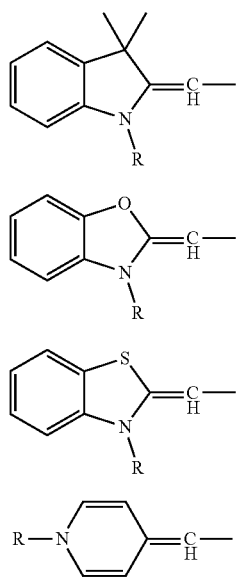

Z in the general formula (1) represents a linking group having a heteroaromatic ring or at least one hydrocarbon group selected from the group consisting of an aromatic ring, a vinylene group (—CH=CH—), or an ethynylene group (—C≡C—), as described above. The linking group Z is not particularly limited, and is preferably a moiety that may be conjugated with a thiazole ring (the thiazole ring shown in the general formula (1)). In addition, the linking group Z is preferably a linking group having at least a structure represented by the following general formula (4):

[Chemical formula 7]

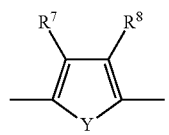

(4)

wherein $R^7$ and $R^8$ each independently represent a hydrogen atom, a substituted or unsubstituted, linear or branched alkyl group, or a substituted or unsubstituted, linear or branched alkoxy group, and $R^7$ and $R^8$ may be linked to each other to form a ring. When $R^7$ and $R^8$ are linked to each other to form a ring, the formed ring is preferably a five or more-membered ring. For example, when $R^7$ and $R^8$ are linked to each other to form a ring, the formed ring may be a six or more-membered ring. Examples of the substituted or unsubstituted alkyl group include alkyl groups having 1 to 8 carbon atoms, such as a methyl group, an ethyl group, a propyl group, a n-butyl group, a pentyl group, a hexyl group, a heptyl group, and an octyl group. Examples of the substituent bonded to the alkyl group include a hydroxy group and alkoxy groups. Examples of the alkoxy group include alkoxy groups having 1 to 4 carbon atoms, such as a methoxy group, an ethoxy group, a propoxy group, and a butoxy group.

In the general formula (4), Y represents an oxygen atom, a sulfur atom, or NRa, and Ra represents a hydrogen atom, a substituted or unsubstituted, linear or branched alkyl group, or a substituted or unsubstituted aryl group. Examples of the substituted or unsubstituted alkyl group include alkyl groups having 1 to 8 carbon atoms, such as a methyl group, an ethyl group, a propyl group, a n-butyl group, a pentyl group, a hexyl group, a heptyl group, and an octyl group, and aralkyl groups, such as a benzyl group. Examples of the substituent bonded to the alkyl group include a hydroxy group, alkoxy groups (for example, alkoxy groups having 1 to 4 carbon atoms), and a phenyl group. Examples of the substituted or unsubstituted aryl group include substituted or unsubstituted aryl groups having 6 to 22 carbon atoms, such as a phenyl group, a tolyl group, a 4-t-butylphenyl group, a 3,5-di-t-butylphenyl group, a 4-methoxyphenyl group, and a 4-(N,N-dimethylamino) phenyl group. Examples of the substituent bonded to the aryl group include alkyl groups (for example, alkyl groups having 1 to 8 carbon atoms), a hydroxy group, alkoxy groups (for example, alkoxy groups having 1 to 4 carbon atoms), and N,N-dialkylamino groups (the alkyl group used therein is, for example, an alkyl group having 1 to 8 carbon atoms).

Specific examples of the linking group Z are shown in the chemical formulae (Z1) to (Z29), but are not limited to these. Chemical formulae (Z1) to (Z27) are each a divalent group having bonds in a heteroaromatic ring or aromatic ring. When a plurality of the heteroaromatic rings or aromatic rings are present, carbons that compose the rings are directly bonded to each other, or the rings are bonded to each other by forming a condensed ring. In addition, a moiety which is formed by linking a plurality of those linking groups may be used.

[Chemical formula 8]
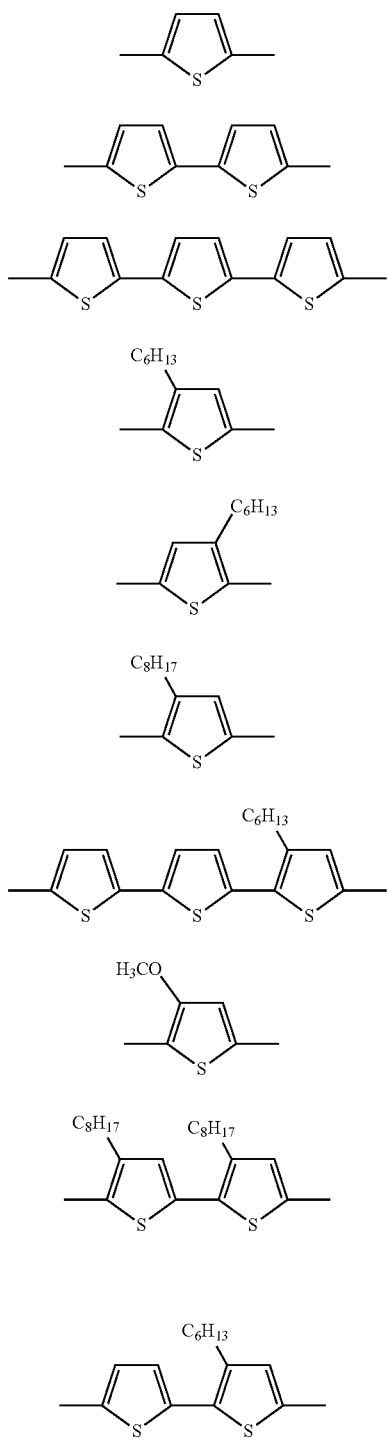
[Chemical formula 9]
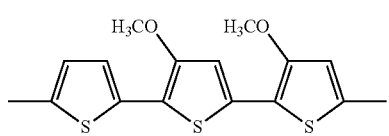
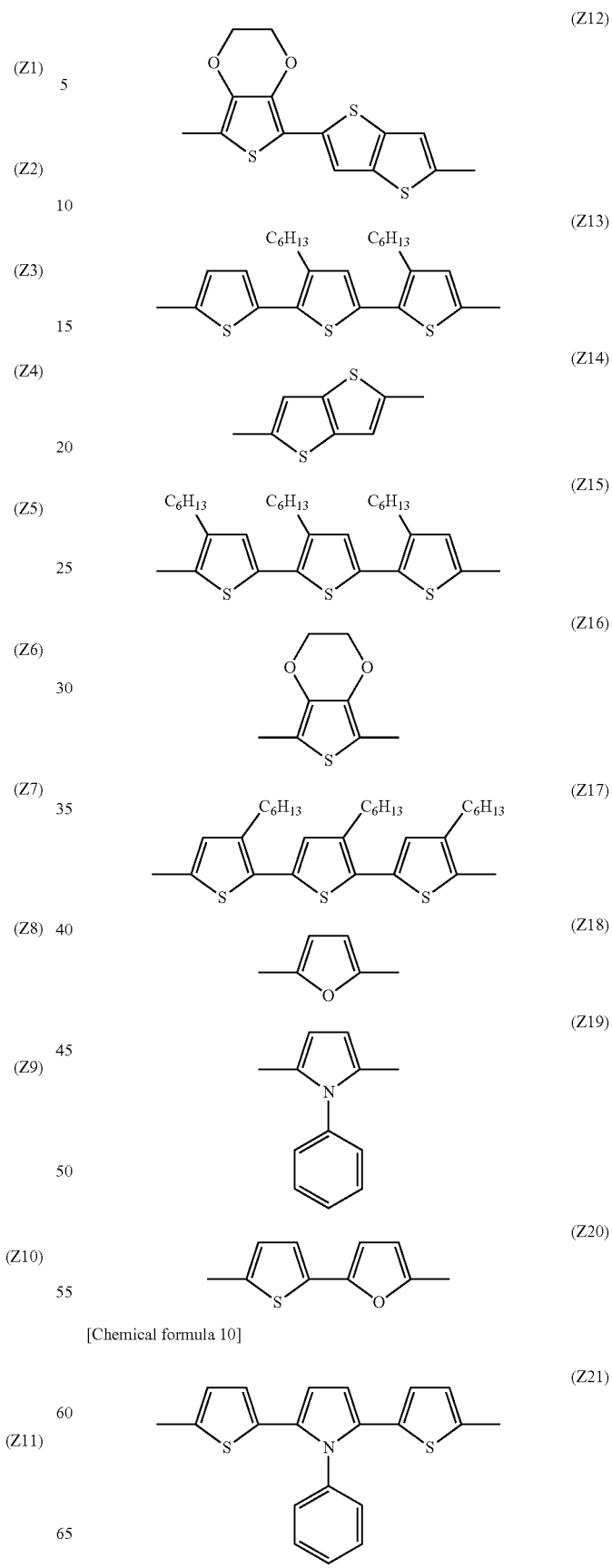
[Chemical formula 10]

(Z22) 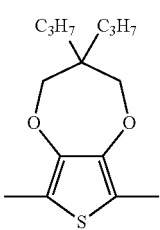

(Z23) 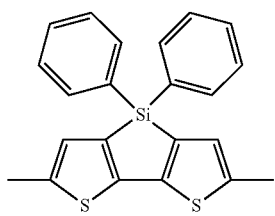

(Z24) 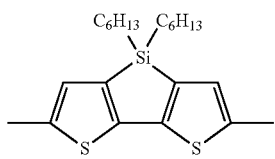

(Z25) 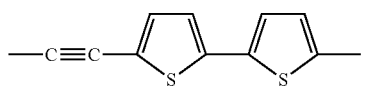

(Z26) 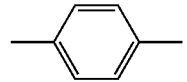

(Z27) 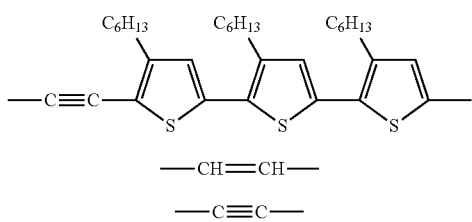

(Z28) —CH=CH—

(Z29) —C≡C—

Examples of the combination of D and Z in the thiazole-based compound represented by the general formula (1), a tautomer or stereoisomer thereof, or a salt thereof include the following (a to o)-(1 to 29).

TABLE 1

Table 1-a

| No. | Moiety D | Z |
|---|---|---|
| a-1 | Formula (2) | Z1 |
| a-2 | Formula (2) | Z2 |
| a-3 | Formula (2) | Z3 |
| a-4 | Formula (2) | Z4 |
| a-5 | Formula (2) | Z5 |
| a-6 | Formula (2) | Z6 |
| a-7 | Formula (2) | Z7 |
| a-8 | Formula (2) | Z8 |
| a-9 | Formula (2) | Z9 |
| a-10 | Formula (2) | Z10 |
| a-11 | Formula (2) | Z11 |
| a-12 | Formula (2) | Z12 |
| a-13 | Formula (2) | Z13 |
| a-14 | Formula (2) | Z14 |

TABLE 1-continued

Table 1-a

| No. | Moiety D | Z |
|---|---|---|
| a-15 | Formula (2) | Z15 |
| a-16 | Formula (2) | Z16 |
| a-17 | Formula (2) | Z17 |
| a-18 | Formula (2) | Z18 |
| a-19 | Formula (2) | Z19 |
| a-20 | Formula (2) | Z20 |
| a-21 | Formula (2) | Z21 |
| a-22 | Formula (2) | Z22 |
| a-23 | Formula (2) | Z23 |
| a-24 | Formula (2) | Z24 |
| a-25 | Formula (2) | Z25 |
| a-26 | Formula (2) | Z26 |
| a-27 | Formula (2) | Z27 |
| a-28 | Formula (2) | Z28 |
| a-29 | Formula (2) | Z29 |

TABLE 2

Table 1-b

| No. | Moiety D | Z |
|---|---|---|
| b-1 | Formula (3) | Z1 |
| b-2 | Formula (3) | Z2 |
| b-3 | Formula (3) | Z3 |
| b-4 | Formula (3) | Z4 |
| b-5 | Formula (3) | Z5 |
| b-6 | Formula (3) | Z6 |
| b-7 | Formula (3) | Z7 |
| b-8 | Formula (3) | Z8 |
| b-9 | Formula (3) | Z9 |
| b-10 | Formula (3) | Z10 |
| b-11 | Formula (3) | Z11 |
| b-12 | Formula (3) | Z12 |
| b-13 | Formula (3) | Z13 |
| b-14 | Formula (3) | Z14 |
| b-15 | Formula (3) | Z15 |
| b-16 | Formula (3) | Z16 |
| b-17 | Formula (3) | Z17 |
| b-18 | Formula (3) | Z18 |
| b-19 | Formula (3) | Z19 |
| b-20 | Formula (3) | Z20 |
| b-21 | Formula (3) | Z21 |
| b-22 | Formula (3) | Z22 |
| b-23 | Formula (3) | Z23 |
| b-24 | Formula (3) | Z24 |
| b-25 | Formula (3) | Z25 |
| b-26 | Formula (3) | Z26 |
| b-27 | Formula (3) | Z27 |
| b-28 | Formula (3) | Z28 |
| b-29 | Formula (3) | Z29 |

TABLE 3

Table 1-c

| No. | Moiety D | Z |
|---|---|---|
| c-1 | D1 | Z1 |
| c-2 | D1 | Z2 |
| c-3 | D1 | Z3 |
| c-4 | D1 | Z4 |
| c-5 | D1 | Z5 |
| c-6 | D1 | Z6 |
| c-7 | D1 | Z7 |

TABLE 3-continued

Table 1-c

| No. | Moiety D | Moiety Z |
|---|---|---|
| c-8 | D1 | Z8 |
| c-9 | D1 | Z9 |
| c-10 | D1 | Z10 |
| c-11 | D1 | Z11 |
| c-12 | D1 | Z12 |
| c-13 | D1 | Z13 |
| c-14 | D1 | Z14 |
| c-15 | D1 | Z15 |
| c-16 | D1 | Z16 |
| c-17 | D1 | Z17 |
| c-18 | D1 | Z18 |
| c-19 | D1 | Z19 |
| c-20 | D1 | Z20 |
| c-21 | D1 | Z21 |
| c-22 | D1 | Z22 |
| c-23 | D1 | Z23 |
| c-24 | D1 | Z24 |
| c-25 | D1 | Z25 |
| c-26 | D1 | Z26 |
| c-27 | D1 | Z27 |
| c-28 | D1 | Z28 |
| c-29 | D1 | Z29 |

TABLE 4

Table 1-d

| No. | Moiety D | Moiety Z |
|---|---|---|
| d-1 | D2 | Z1 |
| d-2 | D2 | Z2 |
| d-3 | D2 | Z3 |
| d-4 | D2 | Z4 |
| d-5 | D2 | Z5 |
| d-6 | D2 | Z6 |
| d-7 | D2 | Z7 |
| d-8 | D2 | Z8 |
| d-9 | D2 | Z9 |
| d-10 | D2 | Z10 |
| d-11 | D2 | Z11 |
| d-12 | D2 | Z12 |
| d-13 | D2 | Z13 |
| d-14 | D2 | Z14 |
| d-15 | D2 | Z15 |
| d-16 | D2 | Z16 |
| d-17 | D2 | Z17 |
| d-18 | D2 | Z18 |
| d-19 | D2 | Z19 |
| d-20 | D2 | Z20 |
| d-21 | D2 | Z21 |
| d-22 | D2 | Z22 |
| d-23 | D2 | Z23 |
| d-24 | D2 | Z24 |
| d-25 | D2 | Z25 |
| d-26 | D2 | Z26 |
| d-27 | D2 | Z27 |
| d-28 | D2 | Z28 |
| d-29 | D2 | Z29 |

TABLE 5

Table 1-e

| No. | Moiety D | Moiety Z |
|---|---|---|
| e-1 | D3 | Z1 |
| e-2 | D3 | Z2 |
| e-3 | D3 | Z3 |
| e-4 | D3 | Z4 |
| e-5 | D3 | Z5 |
| e-6 | D3 | Z6 |
| e-7 | D3 | Z7 |
| e-8 | D3 | Z8 |
| e-9 | D3 | Z9 |
| e-10 | D3 | Z10 |
| e-11 | D3 | Z11 |
| e-12 | D3 | Z12 |
| e-13 | D3 | Z13 |
| e-14 | D3 | Z14 |
| e-15 | D3 | Z15 |
| e-16 | D3 | Z16 |
| e-17 | D3 | Z17 |
| e-18 | D3 | Z18 |
| e-19 | D3 | Z19 |
| e-20 | D3 | Z20 |
| e-21 | D3 | Z21 |
| e-22 | D3 | Z22 |
| e-23 | D3 | Z23 |
| e-24 | D3 | Z24 |
| e-25 | D3 | Z25 |
| e-26 | D3 | Z26 |
| e-27 | D3 | Z27 |
| e-28 | D3 | Z28 |
| e-29 | D3 | Z29 |

TABLE 6

Table 1-f

| No. | Moiety D | Moiety Z |
|---|---|---|
| f-1 | D4 | Z1 |
| f-2 | D4 | Z2 |
| f-3 | D4 | Z3 |
| f-4 | D4 | Z4 |
| f-5 | D4 | Z5 |
| f-6 | D4 | Z6 |
| f-7 | D4 | Z7 |
| f-8 | D4 | Z8 |
| f-9 | D4 | Z9 |
| f-10 | D4 | Z10 |
| f-11 | D4 | Z11 |
| f-12 | D4 | Z12 |
| f-13 | D4 | Z13 |
| f-14 | D4 | Z14 |
| f-15 | D4 | Z15 |
| f-16 | D4 | Z16 |
| f-17 | D4 | Z17 |
| f-18 | D4 | Z18 |
| f-19 | D4 | Z19 |
| f-20 | D4 | Z20 |
| f-21 | D4 | Z21 |
| f-22 | D4 | Z22 |
| f-23 | D4 | Z23 |
| f-24 | D4 | Z24 |
| f-25 | D4 | Z25 |
| f-26 | D4 | Z26 |
| f-27 | D4 | Z27 |
| f-28 | D4 | Z28 |
| f-29 | D4 | Z29 |

TABLE 7

Table 1-g

| No. | Moiety D | Moiety Z |
|---|---|---|
| g-1 | D5 | Z1 |
| g-2 | D5 | Z2 |
| g-3 | D5 | Z3 |
| g-4 | D5 | Z4 |
| g-5 | D5 | Z5 |
| g-6 | D5 | Z6 |
| g-7 | D5 | Z7 |
| g-8 | D5 | Z8 |
| g-9 | D5 | Z9 |
| g-10 | D5 | Z10 |
| g-11 | D5 | Z11 |
| g-12 | D5 | Z12 |
| g-13 | D5 | Z13 |
| g-14 | D5 | Z14 |
| g-15 | D5 | Z15 |
| g-16 | D5 | Z16 |
| g-17 | D5 | Z17 |
| g-18 | D5 | Z18 |
| g-19 | D5 | Z19 |
| g-20 | D5 | Z20 |
| g-21 | D5 | Z21 |
| g-22 | D5 | Z22 |
| g-23 | D5 | Z23 |
| g-24 | D5 | Z24 |
| g-25 | D5 | Z25 |
| g-26 | D5 | Z26 |
| g-26 | D5 | Z27 |
| g-28 | D5 | Z28 |
| g-29 | D5 | Z29 |

TABLE 8

Table 1-h

| No. | Moiety D | Moiety Z |
|---|---|---|
| h-1 | D6 | Z1 |
| h-2 | D6 | Z2 |
| h-3 | D6 | Z3 |
| h-4 | D6 | Z4 |
| h-5 | D6 | Z5 |
| h-6 | D6 | Z6 |
| h-7 | D6 | Z7 |
| h-8 | D6 | Z8 |
| h-9 | D6 | Z9 |
| h-10 | D6 | Z10 |
| h-11 | D6 | Z11 |
| h-12 | D6 | Z12 |
| h-13 | D6 | Z13 |
| h-14 | D6 | Z14 |
| h-15 | D6 | Z15 |
| h-16 | D6 | Z16 |
| h-17 | D6 | Z17 |
| h-18 | D6 | Z18 |
| h-19 | D6 | Z19 |
| h-20 | D6 | Z20 |
| h-21 | D6 | Z21 |
| h-22 | D6 | Z22 |
| h-23 | D6 | Z23 |
| h-24 | D6 | Z24 |
| h-25 | D6 | Z25 |
| h-26 | D6 | Z26 |
| h-27 | D6 | Z27 |
| h-28 | D6 | Z28 |
| h-29 | D6 | Z29 |

TABLE 9

Table 1-i

| No. | Moiety D | Moiety Z |
|---|---|---|
| i-1 | D7 | Z1 |
| i-2 | D7 | Z2 |
| i-3 | D7 | Z3 |
| i-4 | D7 | Z4 |
| i-5 | D7 | Z5 |
| i-6 | D7 | Z6 |
| i-7 | D7 | Z7 |
| i-8 | D7 | Z8 |
| i-9 | D7 | Z9 |
| i-10 | D6 | Z10 |
| i-11 | D7 | Z11 |
| i-12 | D7 | Z12 |
| i-13 | D7 | Z13 |
| i-14 | D7 | Z14 |
| i-15 | D7 | Z15 |
| i-16 | D7 | Z16 |
| i-17 | D7 | Z17 |
| i-18 | D7 | Z18 |
| i-19 | D7 | Z19 |
| i-20 | D7 | Z20 |
| i-21 | D7 | Z21 |
| i-22 | D7 | Z22 |
| i-23 | D7 | Z23 |
| i-24 | D7 | Z24 |
| i-25 | D7 | Z25 |
| i-26 | D7 | Z26 |
| i-27 | D7 | Z27 |
| i-28 | D7 | Z28 |
| i-29 | D7 | Z29 |

TABLE 10

Table 1-j

| No. | Moiety D | Moiety Z |
|---|---|---|
| j-1 | D8 | Z1 |
| j-2 | D8 | Z2 |
| j-3 | D8 | Z3 |
| j-4 | D8 | Z4 |
| j-5 | D8 | Z5 |
| j-6 | D8 | Z6 |
| j-7 | D8 | Z7 |
| j-8 | D8 | Z8 |
| j-9 | D8 | Z9 |
| j-10 | D8 | Z10 |
| j-11 | D8 | Z11 |
| j-12 | D8 | Z12 |
| j-13 | D8 | Z13 |
| j-14 | D8 | Z14 |
| j-15 | D8 | Z15 |
| j-16 | D8 | Z16 |
| j-17 | D8 | Z17 |
| j-18 | D8 | Z18 |
| j-19 | D8 | Z19 |
| j-20 | D8 | Z20 |
| j-21 | D8 | Z21 |
| j-22 | D8 | Z22 |
| j-23 | D8 | Z23 |
| j-24 | D8 | Z24 |
| j-25 | D8 | Z25 |
| j-26 | D8 | Z26 |
| j-27 | D8 | Z27 |
| j-28 | D8 | Z28 |
| j-29 | D8 | Z29 |

TABLE 11

Table 1-k

| No. | Moiety D | Z |
|---|---|---|
| k-1 | D9 | Z1 |
| k-2 | D9 | Z2 |
| k-3 | D9 | Z3 |
| k-4 | D9 | Z4 |
| k-5 | D9 | Z5 |
| k-6 | D9 | Z6 |
| k-7 | D9 | Z7 |
| k-8 | D9 | Z8 |
| k-9 | D9 | Z9 |
| k-10 | D9 | Z10 |
| k-11 | D9 | Z11 |
| k-12 | D9 | Z12 |
| k-13 | D9 | Z13 |
| k-14 | D9 | Z14 |
| k-15 | D9 | Z15 |
| k-16 | D9 | Z16 |
| k-17 | D9 | Z17 |
| k-18 | D9 | Z18 |
| k-19 | D9 | Z19 |
| k-20 | D9 | Z20 |
| k-21 | D9 | Z21 |
| k-22 | D9 | Z22 |
| k-23 | D9 | Z23 |
| k-24 | D9 | Z24 |
| k-25 | D9 | Z25 |
| k-26 | D9 | Z26 |
| k-27 | D9 | Z27 |
| k-28 | D9 | Z28 |
| k-29 | D9 | Z29 |

TABLE 12

Table 1-l

| No. | Moiety D | Z |
|---|---|---|
| l-1 | D10 | Z1 |
| l-2 | D10 | Z2 |
| l-3 | D10 | Z3 |
| l-4 | D10 | Z4 |
| l-5 | D10 | Z5 |
| l-6 | D10 | Z6 |
| l-7 | D10 | Z7 |
| l-8 | D10 | Z8 |
| l-9 | D10 | Z9 |
| l-10 | D10 | Z10 |
| l-11 | D10 | Z11 |
| l-12 | D10 | Z12 |
| l-13 | D10 | Z13 |
| l-14 | D10 | Z14 |
| l-15 | D10 | Z15 |
| l-16 | D10 | Z16 |
| l-17 | D10 | Z17 |
| l-18 | D10 | Z18 |
| l-19 | D10 | Z19 |
| l-20 | D10 | Z20 |
| l-21 | D10 | Z21 |
| l-22 | D10 | Z22 |
| l-23 | D10 | Z23 |
| l-24 | D10 | Z24 |
| l-25 | D10 | Z25 |
| l-26 | D10 | Z26 |
| l-27 | D10 | Z27 |
| l-28 | D10 | Z28 |
| l-29 | D10 | Z29 |

TABLE 13

Table 1-m

| No. | Moiety D | Z |
|---|---|---|
| m-1 | D11 | Z1 |
| m-2 | D11 | Z2 |
| m-3 | D11 | Z3 |
| m-4 | D11 | Z4 |
| m-5 | D11 | Z5 |
| m-6 | D11 | Z6 |
| m-7 | D11 | Z7 |
| m-8 | D11 | Z8 |
| m-9 | D11 | Z9 |
| m-10 | D11 | Z10 |
| m-11 | D11 | Z11 |
| m-12 | D11 | Z12 |
| m-13 | D11 | Z13 |
| m-14 | D11 | Z14 |
| m-15 | D11 | Z15 |
| m-16 | D11 | Z16 |
| m-17 | D11 | Z17 |
| m-18 | D11 | Z18 |
| m-19 | D11 | Z19 |
| m-20 | D11 | Z20 |
| m-21 | D11 | Z21 |
| m-22 | D11 | Z22 |
| m-23 | D11 | Z23 |
| m-24 | D11 | Z24 |
| m-25 | D11 | Z25 |
| m-26 | D11 | Z26 |
| m-27 | D11 | Z27 |
| m-28 | D11 | Z28 |
| m-29 | D11 | Z29 |

TABLE 14

Table 1-n

| No. | Moiety D | Z |
|---|---|---|
| n-1 | D12 | Z1 |
| n-2 | D12 | Z2 |
| n-3 | D12 | Z3 |
| n-4 | D12 | Z4 |
| n-5 | D12 | Z5 |
| n-6 | D12 | Z6 |
| n-7 | D12 | Z7 |
| n-8 | D12 | Z8 |
| n-9 | D12 | Z9 |
| n-10 | D12 | Z10 |
| n-11 | D12 | Z11 |
| n-12 | D12 | Z12 |
| n-13 | D12 | Z13 |
| n-14 | D12 | Z14 |
| n-15 | D12 | Z15 |
| n-16 | D12 | Z16 |
| n-17 | D12 | Z17 |
| n-18 | D12 | Z18 |
| n-19 | D12 | Z19 |
| n-20 | D12 | Z20 |
| n-21 | D12 | Z21 |
| n-22 | D12 | Z22 |

TABLE 14-continued

Table 1-n

| No. | Moiety D | Moiety Z |
|---|---|---|
| n-23 | D12 | Z23 |
| n-24 | D12 | Z24 |
| n-25 | D12 | Z25 |
| n-26 | D12 | Z26 |
| n-27 | D12 | Z27 |
| n-28 | D12 | Z28 |
| n-29 | D12 | Z29 |

TABLE 15

Table 1-o

| No. | Moiety D | Moiety Z |
|---|---|---|
| o-1 | D13 | Z1 |
| o-2 | D13 | Z2 |
| o-3 | D13 | Z3 |
| o-4 | D13 | Z4 |
| o-5 | D13 | Z5 |
| o-6 | D13 | Z6 |
| o-7 | D13 | Z7 |
| o-8 | D13 | Z8 |
| o-9 | D13 | Z9 |
| o-10 | D13 | Z10 |
| o-11 | D13 | Z11 |
| o-12 | D13 | Z12 |
| o-13 | D13 | Z13 |
| o-14 | D13 | Z14 |
| o-15 | D13 | Z15 |
| o-16 | D13 | Z16 |
| o-17 | D13 | Z17 |
| o-18 | D13 | Z18 |
| o-19 | D13 | Z19 |
| o-20 | D13 | Z20 |
| o-21 | D13 | Z21 |
| o-22 | D13 | Z22 |
| o-23 | D13 | Z23 |
| o-24 | D13 | Z24 |
| o-25 | D13 | Z25 |
| o-26 | D13 | Z26 |
| o-27 | D13 | Z27 |
| o-28 | D13 | Z28 |
| o-29 | D13 | Z29 |

The thiazole-based compound represented by the general formula (1) needs to be adsorbed on the surface of the semiconductor layer used in the semiconductor electrode. From this viewpoint, the thiazole-based compound represented by the general formula (1) preferably has a functional group that may be used for adsorption on the surface of the semiconductor layer, and the carboxy group or a salt thereof (—COOM) in the general formula (1) may play the role of the functional group. M represents a hydrogen atom or a salt-forming cation.

Examples of the salt-forming cation M include various cations capable of forming salts with carboxy groups. Examples of such a cation M include an ammonium cation ($NH_4^+$); organic ammonium cations ($A^1A^2A^3A^4N^+$, $A^1$ to $A^4$ each represent a hydrogen atom or an organic group, wherein at least one of them is an organic group) derived from amines; alkali metal ions, such as $Li^+$, $Na^+$, $K^+$, and $Cs^+$; and alkaline-earth metal ions, such as $Mg^{2+}$, $Ca^{2+}$, and $Sr^{2+}$. Examples of the organic group used in the organic ammonium cations include alkyl groups having 1 to 8 carbon atoms, alkenyl groups having 2 to 8 carbon atoms, and aryl groups having 6 to 12 carbon atoms.

The thiazole-based compound of the present invention is particularly preferably a thiazole-based compound represented by the following formula TZ-1, a tautomer or stereoisomer thereof, or a salt thereof.

[Chemical formula 11]

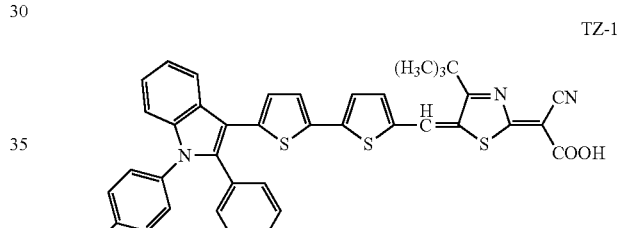

TZ-1

In addition, the thiazole-based compound of the present invention is particularly preferably a thiazole-based compound represented by the following formula TZ-2, a tautomer or stereoisomer thereof, or a salt thereof.

[Chemical formula 12]

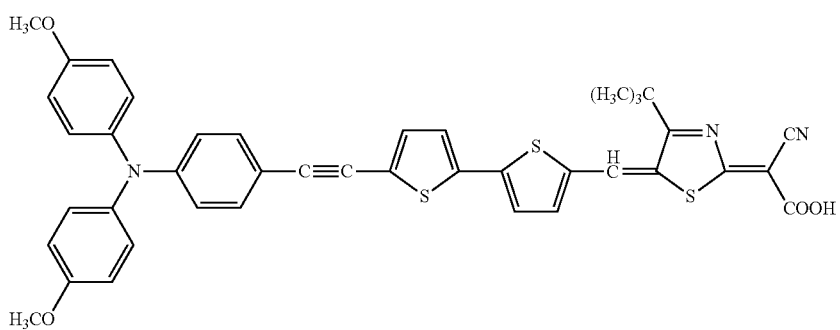

TZ-2

Further, the thiazole-based compound of the present invention is particularly preferably a thiazole-based compound represented by the following formula TZ-3, a tautomer or stereoisomer thereof, or a salt thereof.

[Chemical formula 13]

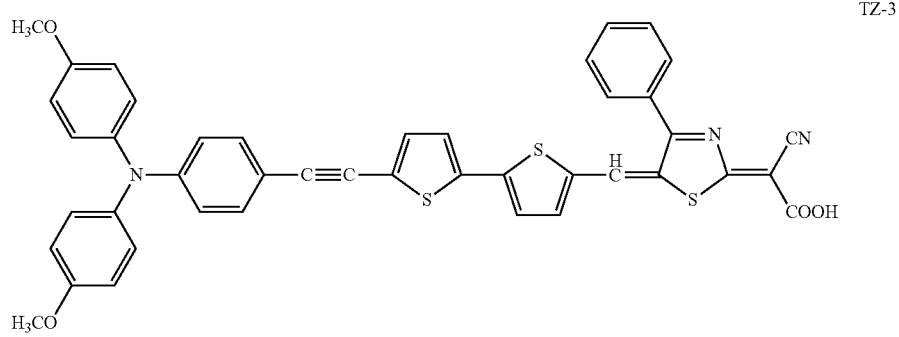

TZ-3

In addition to the thiazole-based compounds represented by the formula TZ-1, formula TZ-2, and formula TZ-3, for example, thiazole-based compounds shown in the following Table 6 and the following formula TZ-4 to formula TZ-6 are particularly preferred. The structure of the thiazole-based compounds shown in the formula TZ-4 to formula TZ-6 is shown in the following Table 6 by the combination of $R^1$, $R^2$, Z, and D in the general formula (1). In addition, these thiazole-based compounds shown in the formula TZ-4 to formula TZ-6 may be easily produced and used in similar manner to the thiazole-based compounds represented by the formula TZ-1, formula TZ-2, and formula TZ-3 by a person skilled in the art without undue trial and error, complicated and sophisticated experiments, or the like by referring to the production method and exemplary embodiments described later. The combination of Z and D in each of the thiazole-based compounds represented by the formula TZ-1 to formula TZ-6 summarized in the following Table 6 may be replaced, for example, by any one of the combinations of Z and D shown in Table 1-a to Table 1-o. In addition, the thiazole-based compound of the general formula (1) according to the present invention is not limited to these examples, and the combination of $R^1$, $R^2$, Z, and D may be any combination included in the scope defined in the general formula (1).

TABLE 16

Table 2

| ID No. of Compound | moiety | | | |
|---|---|---|---|---|
| | $R^1$ | $R^2$ | Z | D |
| TZ-1 | tert-butyl group | H | Z2 | general formula (3)<br>$Ar^4$: 4-methoxyphenyl group<br>$Ar^5$: phenyl group<br>$R^3$~$R^6$: H |
| TZ-2 | tert-butyl group | H | Z2 + Z29 | general formula (2)<br>$Ar^1$: 4-methoxyphenyl group<br>$Ar^2$: 4-methoxyphenyl group<br>$Ar^3$: phenylene group |
| TZ-3 | phenyl group | H | Z2 + Z29 | general formula (2)<br>$Ar^1$: 4-methoxyphenyl group<br>$Ar^2$: 4-methoxyphenyl group<br>$Ar^3$: phenylene group |
| TZ-4 | pheny group | H | Z20 + Z1 | general formula (3)<br>$Ar^4$: 3,5-di-t-butylphenyl group<br>$Ar^5$: phenyl group<br>$R^3$~$R^6$: H |
| TZ-5 | phenyl group | H | Z16 + Z16 | general formula (2)<br>$Ar^1$: 4-t-butylphenyl group<br>$Ar^2$: 4-t-butylphenyl group<br>$Ar^3$: 2,5-thiophenediyl group |
| TZ-6 | phenyl group | H | Z20 + Z20 | general formula (2)<br>$Ar^1$: 4-(α,α-dimethylbenzyl) phenyl group<br>$Ar^2$: 4-(α,α-dimethylbenzyl) phenyl group<br>$Ar^3$: phenylene group |

[Chemical formula 14]

TZ-4

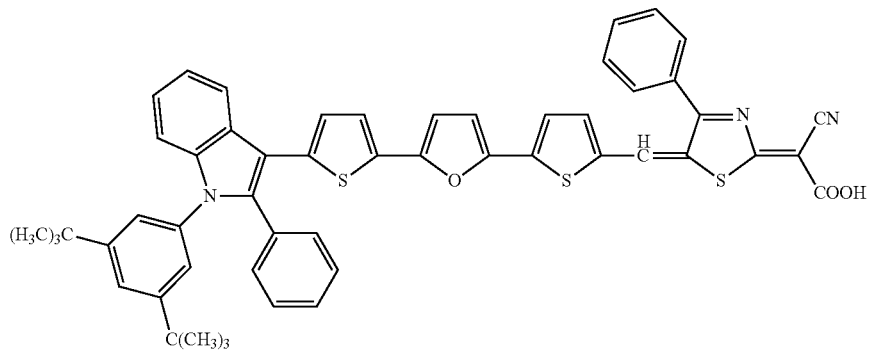

[Chemical formula 15]

TZ-5

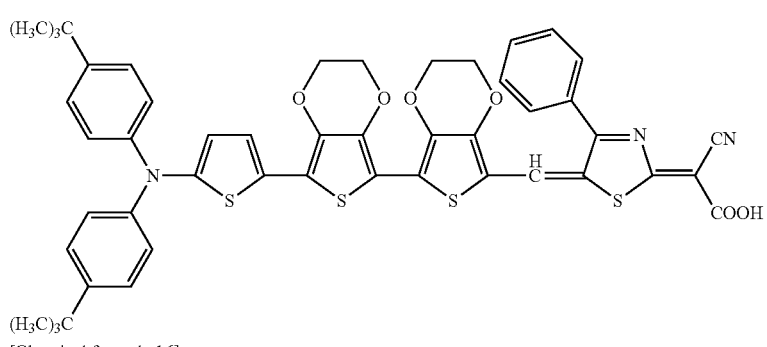

[Chemical formula 16]

TZ-6

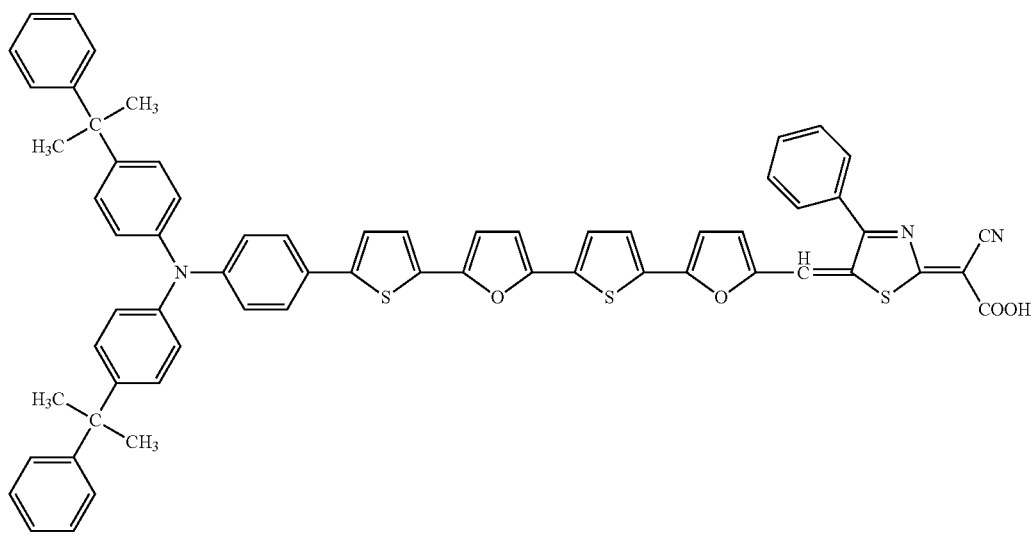

The thiazole-based compound, a tautomer or stereoisomer thereof, or a salt thereof according to the present invention is useful, for example, for a dye for photoelectric conversion having excellent photoelectric conversion performance, but is not limited to this use, and may be used for any use.

<Method for Producing Thiazole-Based Compound>

The method for producing a thiazole-based compound represented by the general formula (1), a tautomer or stereoisomer thereof, or a salt thereof is not particularly limited, and is any method, and may be, for example, the production method shown in the following scheme. The following scheme specifically comprises:

a condensation step of producing a compound represented by the following general formula (III) by the condensation reaction of a compound represented by the following general formula (I) and a compound represented by the following general formula (II); and a hydrolysis (deprotection) step of hydrolyzing (deprotecting) the compound represented by the following general formula (III) to produce a thiazole-based compound represented by the general formula (1).

[Chemical formula 17]

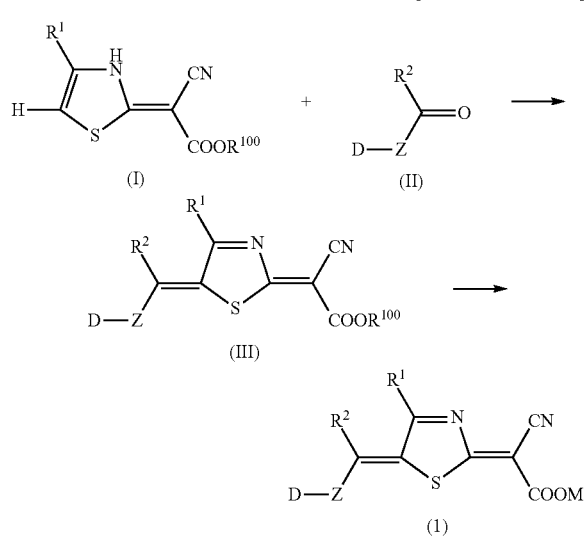

In the general formula (I) and general formula (III),
R¹ is the same as R¹ defined in the general formula (1), and
R¹⁰⁰ is a protecting group, and
in the general formula (II) and general formula (III),
R², D, and Z are the same as R², D, and Z, respectively, defined in the general formula (1).

In the general formula (I) and general formula (III), the protecting group R¹⁰⁰ is preferably a hydrocarbon group. The hydrocarbon group may be linear, branched, or cyclic, may be saturated or unsaturated, and may or may not have a substituent. The number of carbon atoms of the hydrocarbon group is selected, for example, from 1 to 8 when the hydrocarbon group is an acyclic hydrocarbon group. The number of carbon atoms of the hydrocarbon group is selected, for example, from 5 to 9 when the hydrocarbon group is a cyclic hydrocarbon group. The protecting group R¹⁰⁰ is more preferably a substituted or unsubstituted alkyl group. The number of carbon atoms of the alkyl group is selected, for example, from 1 to 8.

The aforementioned production method preferably further comprises a ring-closing step of ring-synthesizing from a compound represented by the following general formula (IV) and a compound represented by the following general formula (V) to produce the compound represented by the general formula (I).

[Chemical formula 18]

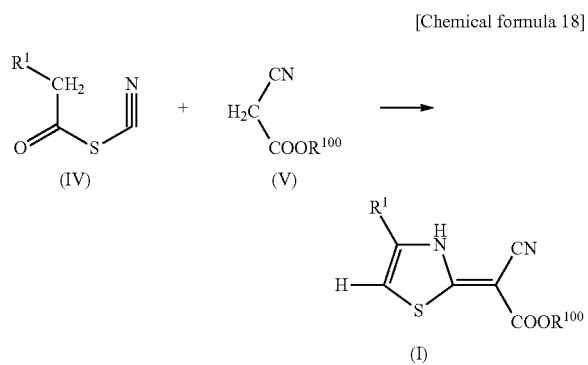

In the general formula (IV), R¹ is the same as R¹ defined in the general formula (I), and
in the general formula (V), R¹⁰⁰ is the same as R¹⁰⁰ defined in the general formula (I).

The production method illustrated above preferably further comprises a thiocyanidation step of reacting a compound represented by the following general formula (VI) with a thiocyanate to produce the compound represented by the general formula (IV).

[Chemical formula 19]

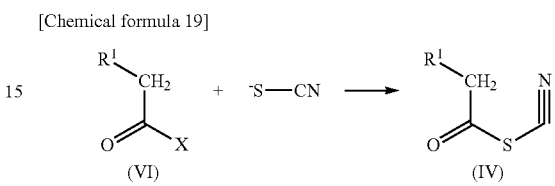

In the general formula (VI), R¹ is the same as R¹ defined in the general formula (IV). In the general formula (VI), X is a halogen atom, for example, Cl, Br, or I.

In the production method explained above, various reaction conditions, such as reaction temperature, reaction time, whether a solvent, a catalyst, and the like are used or not, and their type, in each of the steps are not particularly limited, and, for example, may be appropriately set referring to known similar reactions and the like. The ratio of the amounts of various reagents, solvents, catalysts, and the like used is also not particularly limited, and may be a stoichiometric ratio or an appropriate ratio other than the stoichiometric ratio.

The condensation step is preferably performed in the presence of a solvent. The solvent is also not particularly limited, and examples thereof include a halogenated solvent, such as chloroform, 1,2-dichloroethane and chlorobenzene, and acetonitrile, acetic anhydride, acetic acid or the like. One type may be used, or a plurality of types may be used in combination. The condensation step is preferably performed, for example, in the presence of a catalyst, such as piperidine, triethylamine, sodium acetate, or ammonium acetate. The reaction temperature is not particularly limited, and is selected, for example, from room temperature (for example, 25° C.) to 140° C. The reaction time is also not particularly limited, and is selected, for example, from 1 to 24 hours.

The hydrolysis (deprotection treatment) step is preferably performed under conditions in which acidity, alkalinity, and the like are not strong, so as not to break the thiazole ring. Specifically, for example, the hydrolysis (deprotection treatment) step is preferably performed in the presence of a hydrolysis (deprotection treatment) reagent, such as lithium iodide and lithium bromide. One type of the hydrolysis (deprotection treatment) reagent may be used, or a plurality of types of the hydrolysis (deprotection treatment) reagents may be used in combination. In addition, the hydrolysis (deprotection) step is preferably performed in the presence of a solvent. The solvent is also not particularly limited, and examples thereof include pyridine, lutidine, collidine, and N,N-dimethylformamide. One type may be used, or a plurality of types may be used in combination. The reaction temperature is not particularly limited, and is selected, for example, from 80 to 140° C. The reaction time is also not particularly limited, and is selected, for example, from 1 to 24 hours.

The ring-closing step is preferably performed, for example, in the presence of triethylamine, trioctylamine, or the like. In addition, the ring-closing step is preferably performed in the presence of a solvent. The solvent is also not particularly limited, and examples thereof include dimethylformamide (DMF), dimethylacetamide (DMA), N-methyl-2-pyrrolidone (NMP), ethanol, and methanol. One type may be used, or a plurality of types may be used in combination. The reaction temperature is not particularly limited, and is selected, for example, from room temperature (for example, 25° C.) to 80° C. The reaction time is also not particularly limited, and is selected, for example, from 1 to 24 hours.

In the thiocyanidation step, the counterion (cation) for the thiocyanide ion ($^-$S—CN) is not particularly limited, and any counterion may be selected. Specific examples of the counterion include various metal ions, and the counterion may be selected, for example, from an alkali metal ion, such as $Li^+$, $Na^+$, $K^+$, or $Cs^+$; or an alkaline-earth metal ion, such as $Mg^{2+}$, $Ca^{2+}$, or $Sr^{2+}$. In addition, the thiocyanidation step is preferably performed in the presence of a solvent. The solvent is also not particularly limited, and examples thereof include methanol, ethanol, and isopropyl alcohol. One type may be used, or a plurality of types may be used in combination. The reaction temperature is not particularly limited, and is selected, for example, from room temperature (for example, 25° C.) to 90° C. The reaction time is also not particularly limited, and is selected, for example, from 1 to 12 hours.

<Dye for Photoelectric Conversion>

The dye for photoelectric conversion according to the present invention comprises at least one of the thiazole-based compound, a tautomer or stereoisomer thereof, or a salt thereof according to the present invention, represented by the general formula (1). The thiazole-based compound described above or the like is useful as a dye for photoelectric conversion having excellent photoelectric conversion performance.

<Photoelectric Conversion Device for Photoelectrochemical Cell>

FIG. 1 schematically shows the cross-sectional view of the structure of one example of a photoelectric conversion device for a photoelectrochemical cell according to the present invention. The photoelectric conversion device shown in FIG. 1 comprises a semiconductor electrode 4 for a photoelectrochemical cell, a counter electrode 8, and an electrolyte layer (charge transporting layer) 5 held between the two electrodes. The semiconductor electrode 4 for a photoelectrochemical cell comprises a conductive substrate comprising a light-transmitting substrate 3 and a transparent conductive layer 2, and a semiconductor layer 1. The counter electrode 8 comprises a catalyst layer 6 and a substrate 7. The dye for photoelectric conversion according to the present invention described above is adsorbed on the semiconductor layer 1.

When light is allowed to enter the photoelectric conversion device for a photoelectrochemical cell, the dye for photoelectric conversion that is adsorbed on the semiconductor layer 1 is excited and emits electrons. These electrons are transferred to the conduction band of the semiconductor, and further transferred to the transparent conductive layer 2 by diffusion. The electrons in the transparent conductive layer 2 are transferred to the counter electrode 8 via an external circuit (not shown). The dye for photoelectric conversion that has emitted electrons (oxidized dye) receives electrons from the electrolyte contained in the electrolyte layer 5 (is reduced), and is recovered to the original state, and the dye for photoelectric conversion is regenerated. On the other hand, the electrons transferred to the counter electrode are provided to the electrolyte layer 5 to donate the electrons, and the oxidized electrolyte is reduced. Thereby, the photoelectric conversion device is constructed in such a suitable structure to function as a cell. Taking the photoelectric conversion device for a photoelectrochemical cell shown in FIG. 1 as an example, each component will be described below.

<Semiconductor Electrode for Photoelectrochemical Cell>

The semiconductor electrode 4 for a photoelectrochemical cell comprises the conductive substrate comprising the light-transmitting substrate 3 and the transparent conductive layer 2, and the semiconductor layer 1, as described above. As shown in FIG. 1, the light-transmitting substrate 3, the transparent conductive layer 2, and the semiconductor layer 1 are laminated in this order from the outside toward the inside of the device. The dye for photoelectric conversion (not shown) is adsorbed on the semiconductor layer 1.

<Conductive Substrate>

The conductive substrate that is used to form the semiconductor electrode 4 for a photoelectrochemical cell may be a single-layer structure in which the substrate itself has conductivity, or a two-layer structure composed of a substrate and a conductive layer formed on the substrate. The conductive substrate used in the photoelectric conversion device for the photoelectrochemical cell shown in FIG. 1 has a two-layer structure in which the transparent conductive layer 2 is formed on the light-transmitting substrate 3.

Examples of the substrate used as the basal material for the conductive substrate include glass substrates, plastic substrates, and metal plates. Among them, highly light-transmitting substrates, for example, transparent plastic substrates, are particularly preferred. Examples of the materials of the transparent plastic substrates include polyethylene terephthalate (PET), polyethylene naphthalate (PEN), polycarbonates (PC), polycycloolefins, and polyphenylene sulfide.

In addition, the conductive layer (for example, the transparent conductive layer 2) to be formed on the substrate (for example, the light-transmitting substrate 3) is not particularly limited, and, for example, transparent conductive layers composed of conductive transparent materials, such as Indium-Tin-Oxide (ITO), Fluorine doped Tin Oxide (FTO), Indium Zinc Oxide (IZO), and tin oxide ($SnO_2$), are preferred. The conductive layer to be formed on the substrate may be formed on the entire surface or part of the surface of the substrate in the form of a film. The film thickness of the conductive layer may be appropriately selected, and is preferably selected in the range of about 0.02 μm or more and 10 μm or less. Such a conductive layer may be formed using a usual film formation technique.

A metal lead may also be provided to the conductive substrate used in the embodiment shown in FIG. 1 for the purpose of decreasing the resistance of the conductive substrate. Examples of the material used for the metal lead include metals, such as aluminum, copper, gold, silver, platinum, and nickel. The metal lead may be fabricated by vacuum deposition, sputtering, or the like. It is possible to form the metal lead on the substrate (for example, the light-transmitting substrate 3) and then provide the conductive layer (for example, the transparent conductive layer 2, such as ITO or FTO) on the metal lead. Alternatively, it is possible to provide the conductive layer (for example, the transparent conductive layer 2) on the substrate (for example, the light-transmitting substrate 3) and then fabricate the metal lead on the conductive layer.

For the following description of the embodiment, a description will be given assuming a case (exemplary embodiment) where the conductive substrate of the two-layer structure in which the transparent conductive layer 2 is formed on the light-transmitting substrate 3 is used as the conductive substrate in the semiconductor electrode 4 for a photoelectrochemical cell, but the present invention is not limited to the illustrated exemplary embodiment.

<Semiconductor Layer>

As the material used for forming the semiconductor layer 1, single-element semiconductors, such as silicon and germanium, compound semiconductors, such as metal chalcogenides, semiconductive compounds having a perovskite structure, and the like may be employed.

Examples of the metal chalcogenides include oxides of titanium, tin, zinc, iron, tungsten, indium, zirconium, vanadium, niobium, tantalum, strontium, hafnium, cerium, lanthanum, and the like; sulfides of cadmium, zinc, lead, silver, antimony, bismuth, and the like; selenides of cadmium, lead, and the like; and a telluride of cadmium. Examples of other compound semiconductors include phosphides of zinc, gallium, indium, cadmium, and the like; gallium arsenide; copper-indium-selenide; and copper-indium-sulfide. Examples of the semiconductive compounds having a perovskite structure include commonly known semiconductive compounds, such as barium titanate, strontium titanate, and potassium niobate. The semiconductor materials listed above may be used singly or in combination of two or more.

Among the semiconductor materials listed above, semiconductor materials comprising titanium oxide or zinc oxide are preferred, and semiconductor materials comprising titanium oxide are more preferred, from the viewpoint of conversion efficiency, stability, and safety. Examples of the titanium oxide include various types of titanium oxides, such as anatase type titanium oxide, rutile type titanium oxide, amorphous titanium oxide, metatitanic acid, and orthotitanic acid. In addition, titanium oxide-containing composites may be used. Among those, anatase type titanium oxide is preferred from the viewpoint of further improving the stability of photoelectric conversion.

Examples of the form of the semiconductor layer include porous semiconductor layers obtained by sintering semiconductor fine particles and the like, and semiconductor layers in the shape of thin film obtained by a sol-gel method, a sputtering method, a spray pyrolysis method, or the like. In addition, semiconductor layers in the shape of fiber, and semiconductor layers composed of needle-shape crystals may be used. The forms of the semiconductor layer used therein may be appropriately selected according to the purpose of use of the photoelectric conversion device. Among those, semiconductor layers with a large specific surface area, such as porous semiconductor layers, and semiconductor layers composed of needle-shape crystals, are preferred from the viewpoint of the amount of the dye adsorbed, and the like. Further, porous semiconductor layers formed from semiconductor fine particles are preferred from the viewpoint that the utilization rate of incident light, and the like may be adjusted by the particle diameter of semiconductor fine particles. In addition, the semiconductor layer may be formed in the shape of single layer or in the shape of multilayer. By forming the semiconductor layer in the shape of multilayer, a semiconductor layer with sufficient thickness may be more easily formed. In addition, in the case when the porous semiconductor layer formed from semiconductor fine particles is formed in the shape of multilayer, a plurality of semiconductor layers in which the average particle diameters of semiconductor fine particles used therefor are different from each other may be formed. For example, the average particle diameter of semiconductor fine particles in a semiconductor layer closer to the light incident side (first semiconductor layer) may be set smaller than that of a semiconductor layer farther from the light incident side (second semiconductor layer). In such a case, much light is absorbed by the first semiconductor layer, and light that has passed through the first semiconductor layer is efficiently scattered by the second semiconductor layer, and reflected back to the first semiconductor layer, and the reflected light is also absorbed by the first semiconductor layer. Thus, the net absorbance may be much more improved.

The film thickness of the semiconductor layer is not particularly limited, and may be, for example, selected in the range of 0.5 µm or more and 45 µm or less, from the viewpoint of transmittance, conversion efficiency, and the like. The film thickness of the semiconductor layer is more preferably selected in the range of 1 µm or more and 30 µm or less. The specific surface area of the semiconductor layer may be, for example, selected in the range of 10 $m^2/g$ or more and 200 $m^2/g$ or less, from the viewpoint of adsorbing a large amount of the dye.

In addition, in the case of a structure in which the dye is adsorbed on a porous semiconductor layer, the void ratio of the porous semiconductor layer is preferably selected, for example, in the range of 40% or more and 80% or less, from the viewpoint that ions in the electrolyte diffuse more sufficiently and charge transport is performed. Here, the void ratio is the proportion of the volume of pores in the semiconductor layer to the volume of the semiconductor layer, expressed in percent.

<Method for Forming Semiconductor Layer>

Next, a method for forming the semiconductor layer 1 will be described taking as an example a case where the semiconductor layer 1 is a porous semiconductor layer. The porous semiconductor layer may be formed, for example, as follows. First, semiconductor fine particles are added to a dispersion medium, such as an organic solvent or water, together with an organic compound, such as a resin, and a dispersing agent, to prepare a suspension. Then, the suspension is applied to the conductive substrate (the transparent conductive layer 2 in FIG. 1), and the conductive substrate to which the suspension is applied is dried and fired to obtain a semiconductor layer. When the organic compound is added to the dispersion medium together with the semiconductor fine particles, the organic compound burns during firing, and more sufficient gaps (voids) may be obtained in the porous semiconductor layer. In addition, by adjusting the molecular weight of the organic compound that burns during firing, and the amount of the organic compound added, the void ratio may be changed.

The organic compound is not particularly limited as long as it is dissolved (uniformly dispersed) in the suspension, and may be removed by burning during firing. Examples of the organic compound include polyethylene glycol, cellulose ester resins, cellulose ether resins, epoxy resins, urethane resins, phenolic resins, polycarbonate resins, polyarylate resins, polyvinyl butyral resins, polyester resins, polyvinyl formal resins, and silicon resins, and also include polymers and copolymers of vinyl compounds, such as styrene, vinyl acetate, acrylates, and methacrylates. The type of the organic compound, and the amount of the organic compound blended may be appropriately selected according to the type and state of the semiconductor fine particles used, the composition ratio and total weight of the suspension, and the like. The proportion of the semiconductor fine particles is preferably selected in the range of 10% by mass or more and 40% by mass or less based on the total weight of the entire suspension. When the proportion of the semiconductor fine particles is 10% by mass or more based on the total weight of the entire suspension, the strength of the fabricated porous semiconductor layer may be much more sufficiently high. When the proportion of the semiconductor fine particles is 40% by mass or less based on the total weight of the entire suspension, a porous semiconductor layer with a high void ratio may be much more stably obtained.

As the semiconductor fine particles, particles of a single compound semiconductor or a plurality of compound semiconductors with an appropriate average particle diameter, for example, an average particle diameter of about 1 nm or more and 500 nm or less, and the like may be used. Among them, those with an average particle diameter of about 1 nm or more and 50 nm or less are desired in terms of increasing the specific surface area. In addition, in order to increase the utilization efficiency of incident light, semiconductor particles with a relatively large average particle diameter of about 200 nm or more and 400 nm or less may be added.

Examples of the method for producing the semiconductor fine particles include a sol-gel method, such as a hydrothermal synthesis method, a method using sulfuric acid, and a method using carbothermal chlorination. The method for producing the semiconductor fine particles is not limited as long as it is a method that may produce semiconductor fine particles with the target average particle diameter. From the viewpoint of crystallinity, the semiconductor fine particles are preferably synthesized by the hydrothermal synthesis method.

Examples of the dispersion medium used in the suspension include glyme-type solvents, such as ethylene glycol monomethyl ether; alcohols, such as isopropyl alcohol; mixed solvents, such as isopropyl alcohol/toluene; and water.

The application of the suspension may be performed by a usual application method, such as a doctor blade method, a squeegee method, a spin coating method, or a screen printing method. The conditions of the drying and firing of the coating film performed after the application of the suspension may be, for example, in the air or in an inert gas atmosphere, in the range of about 50° C. or more and 800° C. or less, for about 10 seconds to 12 hours. The drying and firing may be performed one time or a plurality of times at a single temperature, or may be performed a plurality of times with temperature changed.

Other types of semiconductor layers other than porous semiconductor layers may be formed using conventional methods for forming semiconductor layers used in photoelectric conversion devices for photoelectrochemical cells.

<Method for Adsorbing Dye for Photoelectric Conversion>

The dye for photoelectric conversion is such a dye as described above. Examples of the method for adsorbing the dye on the semiconductor layer 1 include a method of immersing a semiconductor substrate (that is, the conductive substrate comprising the semiconductor layer 1) in a solution in which the e dye is dissolved, or a method of applying a solution of the dye to the semiconductor layer 1 for adsorption.

Examples of the solvent of the dye solution include nitrile solvents, such as acetonitrile, propionitrile, and methoxyacetonitrile; alcohol solvents, such as methanol, ethanol, and isopropyl alcohol; ketone solvents, such as acetone, methyl ethyl ketone, methyl isobutyl ketone, and cyclohexanone; ester solvents, such as ethyl acetate and butyl acetate; ether solvents, such as tetrahydrofuran and dioxane; amide solvents, such as N,N-dimethylformamide, N,N-dimethylacetamide, and N-methyl-2-pyrrolidone; halogenated solvents, such as dichloromethane, chloroform, dichloroethane, trichloroethane, and chlorobenzene; hydrocarbon solvents, such as toluene, xylene, and cyclohexane; and water. Those solvents may be used singly or in mixtures of two or more.

When the method of immersing the semiconductor substrate in the dye solution is used, the solution may be stirred, or heated to reflux, or ultrasonic waves may be applied for homogenization while the semiconductor substrate is immersed in the dye solution.

It is desired that after the dye adsorption treatment is performed, washing with a solvent, such as an alcohol, is performed in order to remove the dye remaining without being adsorbed.

The amount of the dye supported may be set, for example, in the range of $1 \times 10^{-10}$ mol/cm$^2$ or more and $1 \times 10^{-4}$ mol/cm$^2$ or less, and is preferably selected in the range of $1 \times 10^{-9}$ mol/cm$^2$ or more and $9.0 \times 10^{-6}$ mol/cm$^2$ or less. In the case when selected in such a range, the effect of improving photoelectric conversion efficiency may be obtained economically and sufficiently.

In addition, in order to widen as much as possible the wavelength region in which photoelectric conversion may be performed, and increase conversion efficiency, two or more dyes for photoelectric conversion may be used in combination. In such a case, the type and proportion of the dyes to be blended are preferably appropriately selected considering the absorption wavelength region and absorption intensity (molar absorption coefficient) of the dyes. In addition, in order to suppress a decrease in conversion efficiency due to the aggregation of the dyes, an additive may be used in combination when the dye is adsorbed. Examples of such an additive include steroid compounds having a carboxy group (for example, deoxycholic acid, cholic acid, and chenodeoxycholic acid).

<Counter Electrode>

The counter electrode 8 in the embodiment shown in FIG. 1 has the catalyst layer 6 on the substrate 7. In this photoelectric conversion device for a photoelectrochemical cell, holes generated from the dye adsorbed on the semiconductor layer 1 due to the incidence of light are carried to the counter electrode 8 through the electrolyte layer 5. The materials of the counter electrode 8 are not limited as long as it may serve the function of eliminating pair of electron and hole efficiently by recombination.

The catalyst layer 6 may be formed, for example, on the substrate 7, as a deposited metal film, for example, by a vacuum deposition method. The catalyst layer 6 may be, for example, a Pt layer formed on the substrate 7. In addition, the catalyst layer 6 may comprise a nano-carbon material. For example, a paste comprising carbon nanotubes, carbon nanohorns, or carbon fibers may be sintered on a porous insulating film to form the catalyst layer 6. The nano-carbon material has a large specific surface area, and may improve the efficiency of recombination of electron and hole pair.

Examples of the substrate 7 include transparent substrates, such as glass and polymer films, and metal plates (foil). When a light-transmitting counter electrode 8 is fabricated, it may be fabricated by selecting glass with a transparent conductive film as the substrate 7, and forming a film of platinum, carbon, or the like on the glass as the catalyst layer 6 by using a vacuum deposition method or a sputtering method.

<Electrolyte Layer (Charge Transporting Layer)>

The electrolyte layer (charge transporting layer) 5 has the function of transporting to the counter electrode 8 holes generated from the dye adsorbed on the semiconductor layer 1 due to the incidence of light. A charge transporting material is contained in the electrolyte layer 5. As the electrolyte layer 5, electrolytic solutions in which a redox reagent pair is dissolved in an organic solvent, gel electrolytes in which a polymer matrix is impregnated with a liquid in which a redox reagent pair is dissolved in an organic solvent, molten salts containing a redox reagent pair, solid electrolytes, organic hole transporting materials, and the like may be used.

The electrolyte layer may be composed of an electrolyte, a solvent, and additives. Examples of the electrolyte include combinations of $I_2$ with iodides, for instance, metal iodides, such as LiI, NaI, KI, CsI, and CaI$_2$, and iodine salts of quaternary ammonium compounds, such as tetraalkylammonium iodides, pyridinium iodide, and imidazolium iodide, combinations of Br$_2$ with bromides, for instance, metal bromides, such as LiBr, NaBr, KBr, CsBr, and CaBr$_2$, and bromine salts of quaternary ammonium compounds, such as tetraalkylammonium bromides and pyridinium bromide, and; metal complexes, such as ferrocyanate-ferricyanates and a ferrocene-ferricinium ion; sulfur compounds, such as sodium polysulfide and alkylthiol-alkyl disulfides; viologen dyes; and hydroquinone-quinones. Among those, a combination of LiI with pyridinium iodide, or a combination of I$_2$ with imidazolium iodide is preferred. In addition, the electrolytes may be used singly or in mixtures of two or more. In addition, as the electrolyte, molten salts that are in a molten state at room temperature may also be used. In such a case, a solvent need not be used.

Examples of the solvent include carbonate solvents, such as ethylene carbonate, diethyl carbonate, dimethyl carbonate, and propylene carbonate; amide solvents, such as N-methyl-2-pyrrolidone and N,N-dimethylformamide; nitrile solvents, such as methoxypropionitrile, propionitrile, methoxyacetonitrile, and acetonitrile; lactone solvents, such as γ-butyrolactone and valerolactone; ether solvents, such as tetrahydrofuran, dioxane, diethyl ether, and ethylene glycol dialkyl ethers; alcohol solvents, such as methanol, ethanol, and isopropyl alcohol; aprotic polar solvents, such as dimethyl sulfoxide and sulfolane; and heterocyclic compounds, such as 2-methyl-3-oxazolidinone and 2-methyl-1,3-dioxolane. Those solvents may be used singly or in mixtures of two or more.

In order to suppress dark current, a basic compound may be added to the electrolyte layer. The type of the basic compound is not particularly limited. Examples thereof include t-butylpyridine, 2-picoline (2-methylpyridine), and 2,6-lutidine. In such a case when the basic compound is added, the concentration of the basic compound added may be selected, for example, in the range of about 0.05 mol/L or more and 2 mol/L or less.

As the electrolyte layer, electrolytes in a solid state may also be used. As the electrolytes in a solid state, gel electrolytes and completely solid electrolytes may be used. As the gel electrolytes, gelling agents to which electrolytes or room temperature molten salts are added, and the like may be used. As the method of gelation, gelation may be performed by a method such as the addition of a polymer or an oil gelling agent, the polymerization of coexisting polyfunctional monomers, or the crosslinking reaction of a polymer. Examples of the polymer that may be used in gelation by the addition of the polymer include polyacrylonitrile and polyvinylidene fluoride. Examples of the oil gelling agent include dibenzylidene-D-sorbitol, cholesterol derivatives, amino acid derivatives, alkylamide derivatives of trans-(1R,2R)-1,2-cyclohexanediamine, alkylurea derivatives, N-octyl-D-gluconamidobenzoate, double-headed amino acid derivatives, and quaternary ammonium salt derivatives.

When gelation is performed by the polymerization of the polyfunctional monomer, the monomer used therefor is preferably a compound having two or more ethylene-type unsaturated groups. Examples thereof include divinylbenzene, ethylene glycol dimethacrylate, ethylene glycol diacrylate, diethylene glycol dimethacrylate, diethylene glycol diacrylate, triethylene glycol dimethacrylate, triethylene glycol diacrylate, pentaerythritol triacrylate, and trimethylolpropane triacrylate. In gelation, a monofunctional monomer other than the polyfunctional monomer may be included. Examples of the monofunctional monomer include acrylamide, N-isopropylacrylamide, esters derived from acrylic acid and α-alkylacrylic acids, such as methyl acrylate and hydroxyethyl acrylate; amides; esters derived from maleic acid and fumaric acid, such as dimethyl maleate, diethyl fumarate, and dibutyl maleate; dienes, such as butadiene, isoprene, and cyclopentadiene; aromatic vinyl compounds, such as styrene, p-chlorostyrene, and sodium styrenesulfonate; vinyl esters, such as vinyl acetate; nitriles, such as acrylonitrile and methacrylonitrile; vinyl compounds having a nitrogen-containing heteroaromatic ring, such as vinylcarbazole; vinyl compounds having a quaternary ammonium salt; and, in addition, N-vinylformamide, vinylsulfonic acid, vinylidene fluoride, vinyl alkyl ethers, and N-phenylmaleimide. The content ratio of the polyfunctional monomer in the total amount of monomers is selected ¥ preferably in the range of 0.5% by mass or more and 70% by mass or less, more preferably in the range of 1.0% by mass or more and 50% by mass or less.

The polymerization of the monomer for gelation may be performed by a radical polymerization method or the like. The radical polymerization may be performed by heating, light, ultraviolet rays, or electron beams, or electrochemically. Examples of a polymerization initiator used when a crosslinked polymer is formed by heating include azo initiators, such as 2,2'-azobis(isobutyronitrile) and 2,2'-azobis (dimethylvaleronitrile), and peroxide initiators, such as benzoyl peroxide. The amount of the polymerization initiator added is selected preferably in the range of 0.01% by mass or more and 15% by mass or less, more preferably in the range of 0.05% by mass or more and 10% by mass or less, based on the total amount of the monomer.

When gelation is performed by the crosslinking reaction of a polymer, it is desired that a polymer having a reactive group necessary for a crosslinking reaction and a crosslinking agent are used in combination. Preferred crosslinkable reactive groups are nitrogen-containing heterocycles, such as a pyridine ring, an imidazole ring, a thiazole ring, an oxazole ring, a triazole ring, a morpholine ring, a piperidine ring, and a piperazine ring. Examples of preferred crosslinking agents include bi- or more-functional compounds capable of undergoing an electrophilic substitution reaction with a nitrogen atom, such as alkyl halides, aralkyl halides, sulfonates, acid anhydrides, acyl chlorides, and isocyanates.

As the completely solid electrolytes, for example, mixtures of electrolytes and ion-conducting polymer compounds may be used. Examples of these ion-conducting polymer compounds include polar polymer compounds, such as polyethers, polyesters, polyamines, and polysulfides.

As the charge transporting material, for example, inorganic hole transporting materials, such as copper iodide and copper thiocyanide, may be used. The inorganic hole transporting materials may be introduced into the electrode by a method such as a casting method, an application method, a spin coating method, an immersion method, or electrolytic plating.

In the photoelectric conversion device for a photoelectrochemical cell according to the embodiment shown in FIG. 1, organic hole transporting materials may also be used as the charge transporting material. Examples of the organic hole transporting materials include 2,2',7,7'-tetrakis(N,N-di-p-methoxyphenylamine)-9,9'-spirobifluorene (for example, a compound described in Adv. Mater. 2005, 17, 813), aromatic diamines, such as N,N'-diphenyl-N,N'-bis(3-methylphenyl)-(1,1'-biphenyl)-4,4'-diamine, (for example, a compound disclosed in the description of U.S. Pat. No. 4,764,625 A), triphenylamine derivatives (for example, a compound disclosed in JP H04-129271 A), stilbene derivatives (for example, a compound disclosed in JPH02-51162 A), and hydrazone derivatives (for example, a compound disclosed in JPH02-226160 A). The organic hole transporting materials may be introduced into the electrode by a method such as a vacuum deposition method, a casting method, a spin coating method, an immersion method, or an electrolytic polymerization method.

The fabrication of the electrolyte layer 5 may be performed, for example, by the following two methods. One is a method of previously bonding the counter electrode 8 to the semiconductor layer 1 on which the dye for photoelectric conversion is adsorbed, and introducing the electrolyte layer 5 in a liquid state into the gap between them. The other is a method of forming the electrolyte layer 5 directly on the semiconductor layer 1. In the latter case, after the electrolyte layer 5 is formed, the counter electrode 8 is formed on the electrolyte layer 5.

Using the photoelectric conversion device for a photoelectrochemical cell described above, a photoelectrochemical cell may be provided. This photoelectrochemical cell may be preferably used as a solar cell (for example, a dye-sensitized solar cell).

EXAMPLES

The present invention will be described in more detail hereafter by giving the following exemplary embodiments. Each exemplary embodiment illustrated below is one example of the best modes of embodiment according to the present invention, but the technical scope of the present invention is not limited to modes illustrated in such exemplary embodiments.

First Exemplary Embodiment

Synthesis of Thiazole-Based Compound TZ-1

A thiazole-based compound TZ-1 was synthesized according to the following reaction scheme.

[Chemical formula 20]

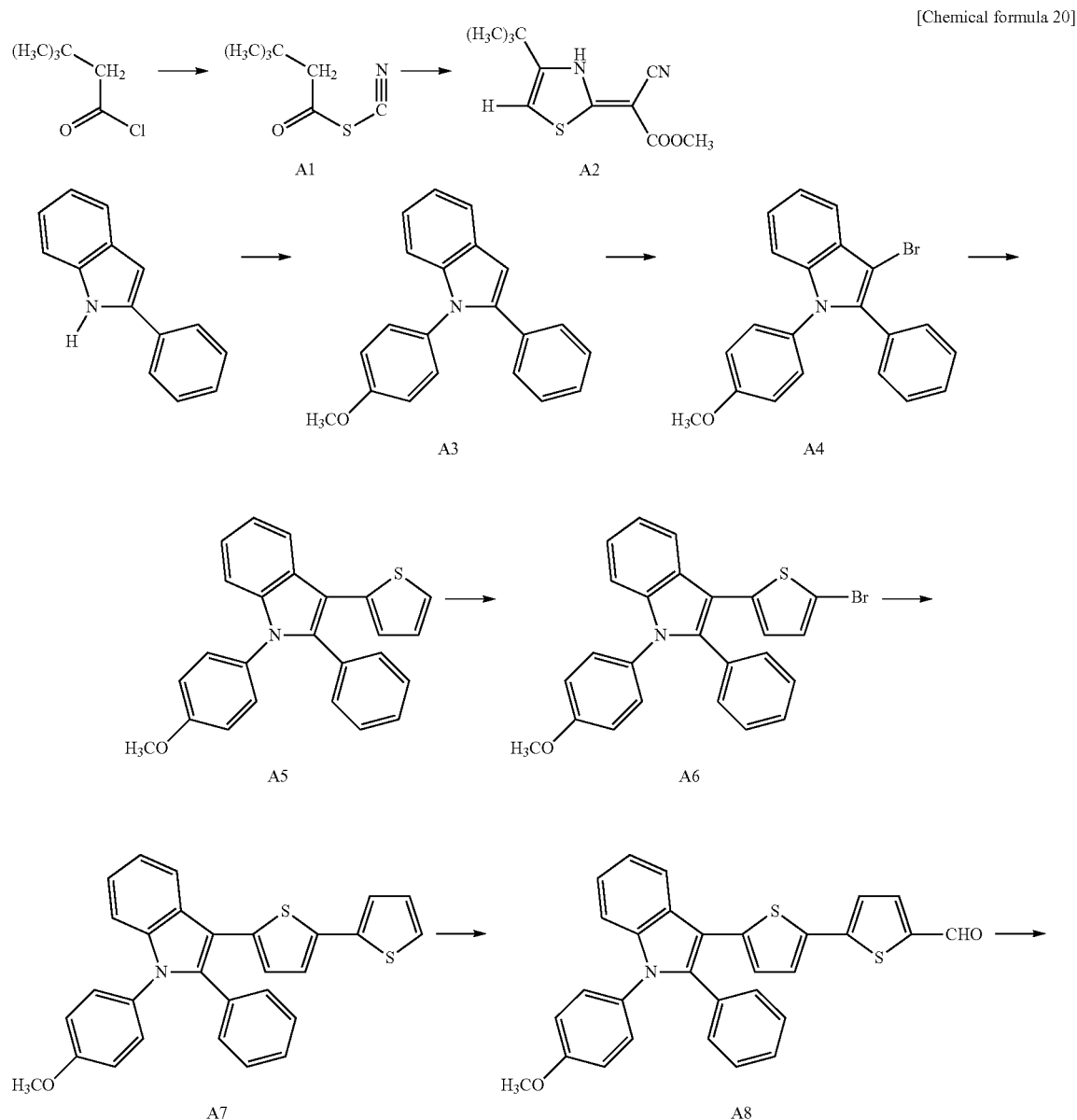

-continued

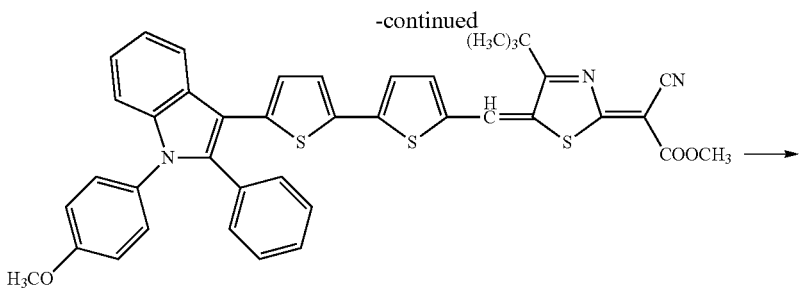

A9

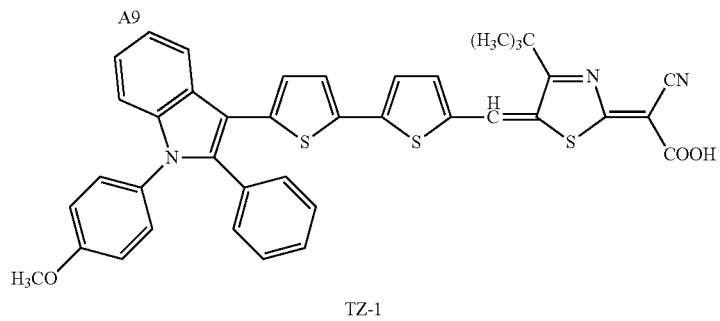

TZ-1

11.85 g of 1-chloropinacolin and 7.64 g of sodium thiocyanate were dissolved in 80 mL of ethanol, and the solution was heated to reflux for 3 hours. The solution was allowed to cool, and then poured into 600 mL of water. The precipitated crystals were filtered off, and further washed with water to obtain 8.5 g of A1.

Next, 7.36 g of A1 and 10 g of methyl cyanoacetate were dissolved in 15 mL of N,N-dimethylformamide (DMF), and 9.02 g of triethylamine was added thereto. The mixture was stirred overnight at room temperature. The reaction mixture was poured into 400 mL of water comprising 20 mL of acetic acid, and the organic layer was extracted with ethyl acetate, washed with a saline solution, and dried with magnesium sulfate. The solvent was distilled off under reduced pressure, and 50 mL of diethyl ether was added to the residue, followed by stirring and washing to obtain 1.3 g of A2.

5.82 g of 2-phenylindole and 7.38 g of p-iodoanisole were dissolved in 26 mL of toluene, and 11.17 g of tripotassium phosphate, 0.25 g of copper iodide, and 0.57 mL of N,N-dimethylethylenediamine were added thereto. The mixture was heated to reflux for 24 hours. The mixture was allowed to cool, and then, 100 mL of ethyl acetate was added. The insoluble matter was filtered off, and the filtrate was concentrated under reduced pressure. The residue was purified by using a silica gel column (eluent: hexane/chloroform=4/1) to obtain 6.0 g of A3.

Next, 6 g of A3 was dissolved in 200 mL of tetrahydrofuran (THF), and 3.58 g of N-bromosuccinimide (NBS) was added thereto at 5 to 8° C. The mixture was stirred at the temperature for 1 hour. The reaction solvent was distilled off under reduced pressure, and the residue was washed with water, a saturated aqueous solution of sodium hydrogen carbonate, water, and methanol in this order to obtain 7.54 g of A4.

Next, 5.03 g of A4 and 5.95 g of 2-tributyltin thiophene were dissolved in 270 mL of DMF, and 0.737 g of tetrakis (triphenylphosphine)palladium(0) was added thereto. The mixture was stirred at 100° C. for 2 hours. The mixture was allowed to cool, and then, the solvent was distilled off under reduced pressure. The residue was washed with hexane (50 mL×3) and methanol (50 mL×4), and then purified by using a silica gel column (eluent: hexane/chloroform=2/1) to obtain 6.3 g of A5.

Next, 12.7 g of A5 was dissolved in 300 mL of THF, and 5.97 g of NBS was added at 4 to 6° C. The mixture was stirred for 1 hour. The solvent was distilled off under reduced pressure, and the residue was washed with water, a saturated aqueous solution of sodium hydrogen carbonate, water, and methanol in this order to obtain 14.6 g of A6.

Next, 1.387 g of tetrakis(triphenylphosphine)palladium(0) was added to a mixture of 9.21 g of A6, 3.07 g of 2-thiopheneboronic acid, 300 mL of dimethoxyethane, and 20 mL of a 2 mol/L aqueous solution of sodium hydrogen carbonate, and the mixture was heated to reflux for 22 hours. The mixture was allowed to cool, and then, 350 mL of water was added. The precipitated solid was filtered off, and washed with water and methanol. The obtained solid was purified by using a silica gel column (eluent hexane/chloroform=3/1) to obtain 6.9 g of A7.

Next, 2.5 g of A7 was dissolved in 70 mL of THF, and 3.5 mL of n-butyllithium (1.64 mol/L hexane solution) was added at −60° C. The mixture was stirred for 2 hours. 0.63 mL of DMF was dropped thereinto, and the mixture was heated to room temperature, and further stirred for 1 hour. A saturated saline solution was added to the reaction solution, followed by extraction with ethyl acetate and washing with a saturated saline solution. Then, the organic layer was dried with magnesium sulfate. The solvent was distilled off under reduced pressure, and the residue was purified by using a silica gel column (eluent: hexane/chloroform=1/1) to obtain 2.09 g of A8.

Next, 1.0 g of A8 and 0.73 g of A2 were dissolved in 20 mL of chloroform, and 0.43 g of piperidine was added thereto. The mixture was heated to reflux for 10 hours. The mixture was allowed to cool, and then concentrated under reduced pressure. The residue was dissolved in 8 mL of THF, and the solution was dropped into 300 mL of water comprising 1 mL of concentrated hydrochloric acid. The precipitated crystals were filtered off, and washed with water and methanol in this order to obtain 0.92 g of A9.

Next, 0.1 g of A9 was dissolved in 10 mL of pyridine, and 0.19 g of lithium iodide was added thereto. The mixture was stirred at 115° C. for 10 hours. The mixture was allowed to cool, and then dropped into 400 mL of water, and the mixture was made acidic with dilute hydrochloric acid. The precipitated crystals were filtered off, water-washed, and dried. The obtained crystals were purified by using a silica gel column (eluent: ethyl acetate) to obtain 0.03 g of the target thiazole-based compound TZ-1 (yield 31%).

The measurement results of the $^1$H-NMR (THF-d8) of the obtained thiazole-based compound TZ-1 were as described below: δ 8.12 (1H, s), 7.99 (1H, d), 7.63 (1H, d), 7.40 (1H, d), 7.17-7.31 (11H, m), 6.89-6.94 (3H, m), 3.78 (3H, s), 1.58 (9H, s)

Figure 2:
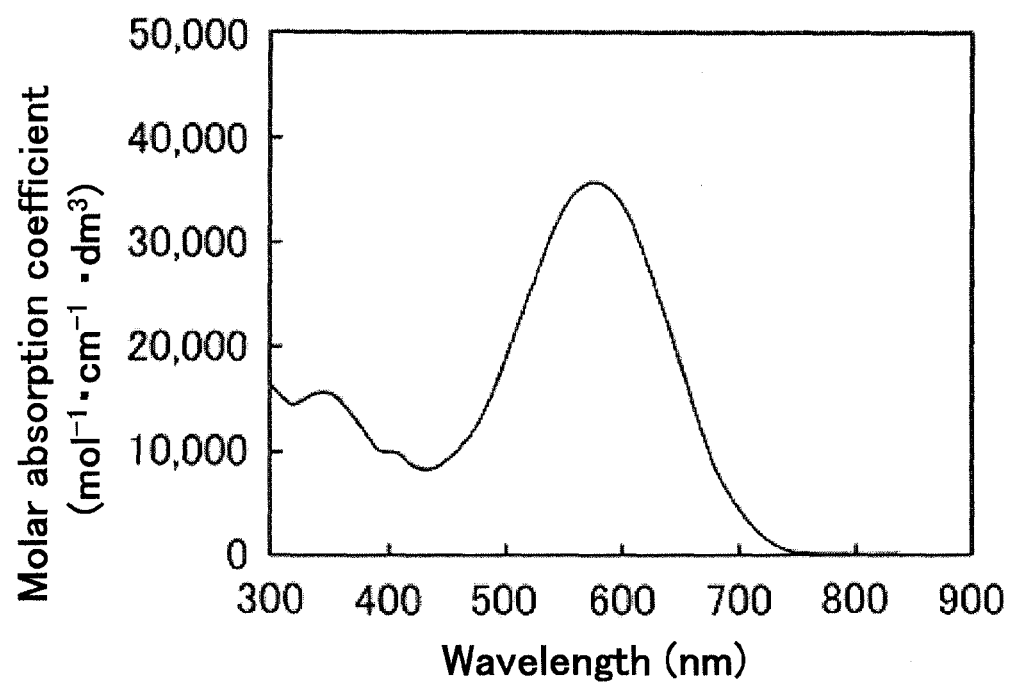
FIG. 2 is a chart showing the absorption spectrum of thiazole-based compound (TZ-1) disclosed in first exemplary embodiment.

In addition, the absorption spectrum of the obtained thiazole-based compound TZ-1 (dye) in THF is shown in FIG. 2. The $\lambda_{max}$ of the thiazole-based compound TZ-1 was 577 nm.

Second Exemplary Embodiment

Synthesis of Thiazole-Based Compound TZ-2

A thiazole-based compound TZ-2 was synthesized according to the following reaction scheme.

[Chemical formula 21]

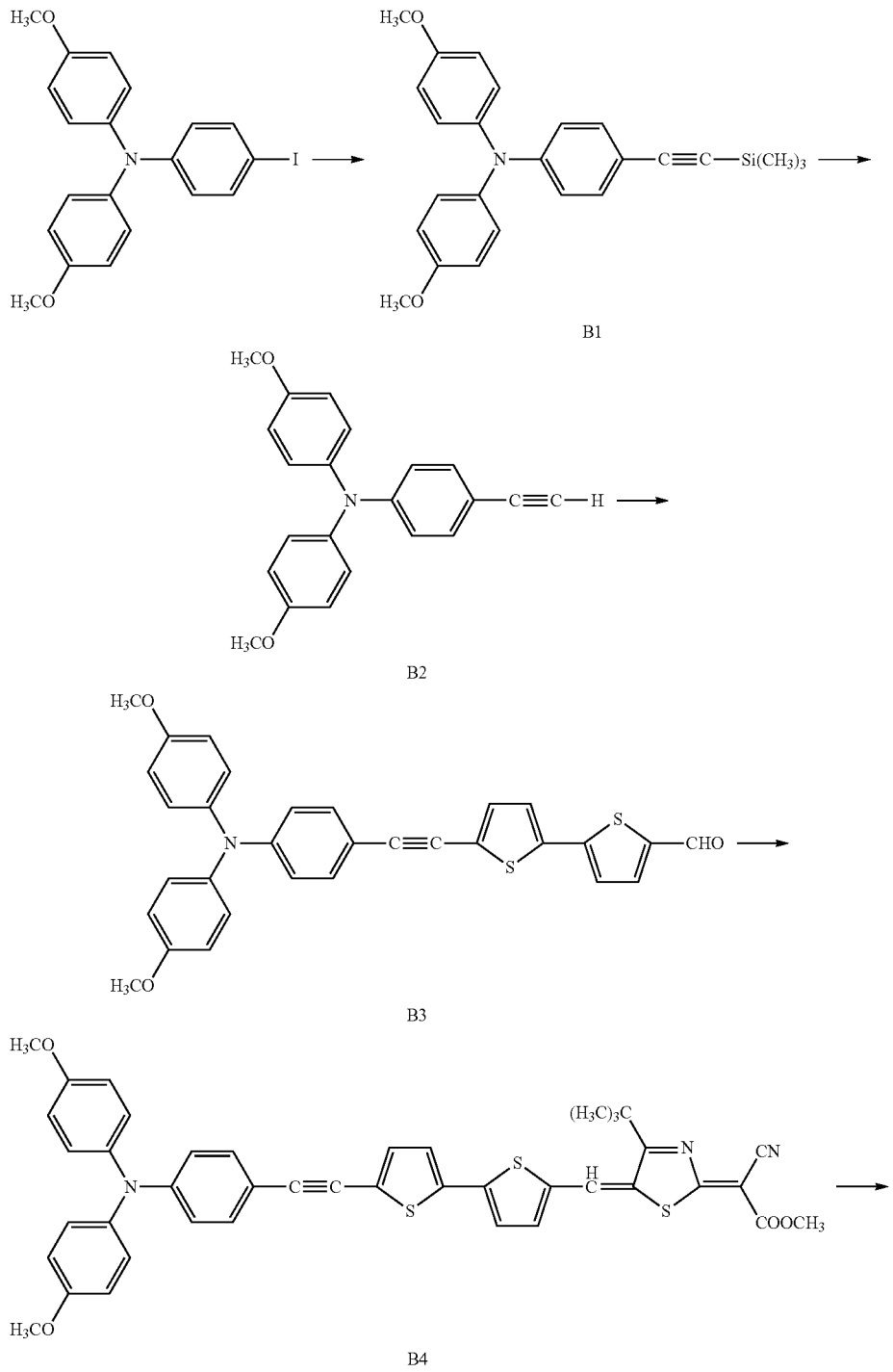

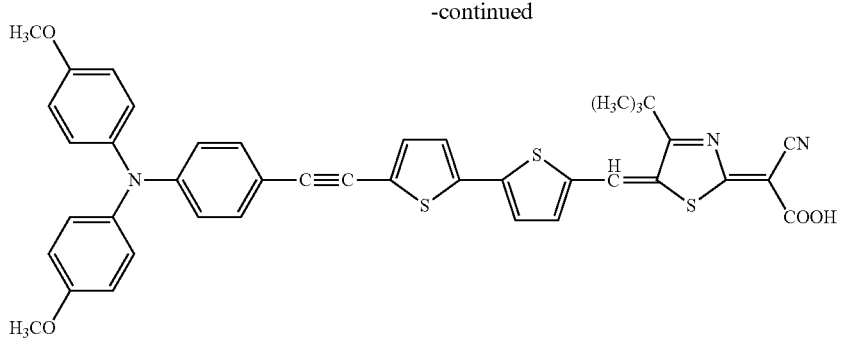

TZ-2

30 g of 4-iodo-4',4"-dimethoxytriphenylamine was dissolved in 630 mL of diethylamine. 317 mg of copper iodide (CuI) and 2.22 g of bis(triphenylphosphine) palladium(II) dichloride were added thereto, and 11.4 mL of trimethylsilylacetylene was further added. The mixture was stirred at 60° C. for 1.5 hours. The mixture was cooled down to room temperature, and then, the solvent was distilled off under reduced pressure. 100 mL of water was added to the residue, followed by extraction with diethyl ether and washing with 100 mL of water. The organic layer was dried with magnesium sulfate. The solvent was distilled off under reduced pressure, and the residue was purified by using a silica gel column (eluent: hexane/chloroform=3/1) to obtain 31 g of a compound B1.

Next, 15.5 g of B1 was dissolved in 100 mL of methanol, and 6.92 g of potassium carbonate was added thereto. The mixture was stirred at room temperature for 1 hour. The mixture was celite-filtered, and the solvent was distilled off under reduced pressure. The residue was purified by using a silica gel column (eluent: hexane/chloroform=3/1) to obtain 7.7 g of A2.

Next, 95.4 mg of triphenylphosphine and 128 mg of bis (triphenylphosphine) palladium(II) dichloride were added to a mixed solution of 1 g of B2, 0.912 g of 5-bromo-5'-formyl-2,2'-bithiophene, and 60 mL of diisopropylamine, and the mixture was heated to reflux for 1 hour. The mixture was cooled down to room temperature, and the solvent was distilled off under reduced pressure. Water was added to the residue, followed by extraction with chloroform. The organic layer was washed with water, and dried with magnesium sulfate, and the solvent was distilled off under reduced pressure. The residue was purified by using a silica gel column (eluent: hexane/toluene=2/8) to obtain 0.285 g of a compound B3 (yield 12%).

Next, 0.8 g of B3 and 0.548 g of A2 synthesized in the first exemplary embodiment were dissolved in 16 mL of chloroform, and 0.33 g of piperidine was added thereto. The mixture was heated to reflux for 10 hours. The mixture was allowed to cool, and then concentrated under reduced pressure. The residue was dissolved in 8 mL of THF, and the solution was dropped into 300 mL of water comprising 0.5 mL of concentrated hydrochloric acid. The precipitated crystals were filtered off, and washed with water and methanol in this order to obtain 0.5 g of B4.

Next, 0.2 g of B4 was dissolved in 15 mL of pyridine, and 0.36 g of lithium iodide was added thereto. The mixture was stirred at 115° C. for 6 hours. The mixture was allowed to cool, and then dropped into 400 mL of water, and the mixture was made acidic with dilute hydrochloric acid. The precipitated crystals were filtered off, water-washed, and dried. The obtained crystals were purified by using a silica gel column (eluent: ethyl acetate/methanol=10/1) to obtain 0.035 g of the target thiazole-based compound TZ-2 (yield 18%).

The measurement results of the $^1$H-NMR (THF-d8) of the obtained thiazole-based compound TZ-2 were as described below: δ 8.16 (1H, s), 7.63 (1H, s), 7.39-7.46 (2H, m), 7.25 (2H, d), 7.18 (1H, s), 7.07 (4H, d), 6.87 (4H, d), 6.79 (4H, d), 3.76 (6H, s), 1.57 (9H, s)

Figure 3:
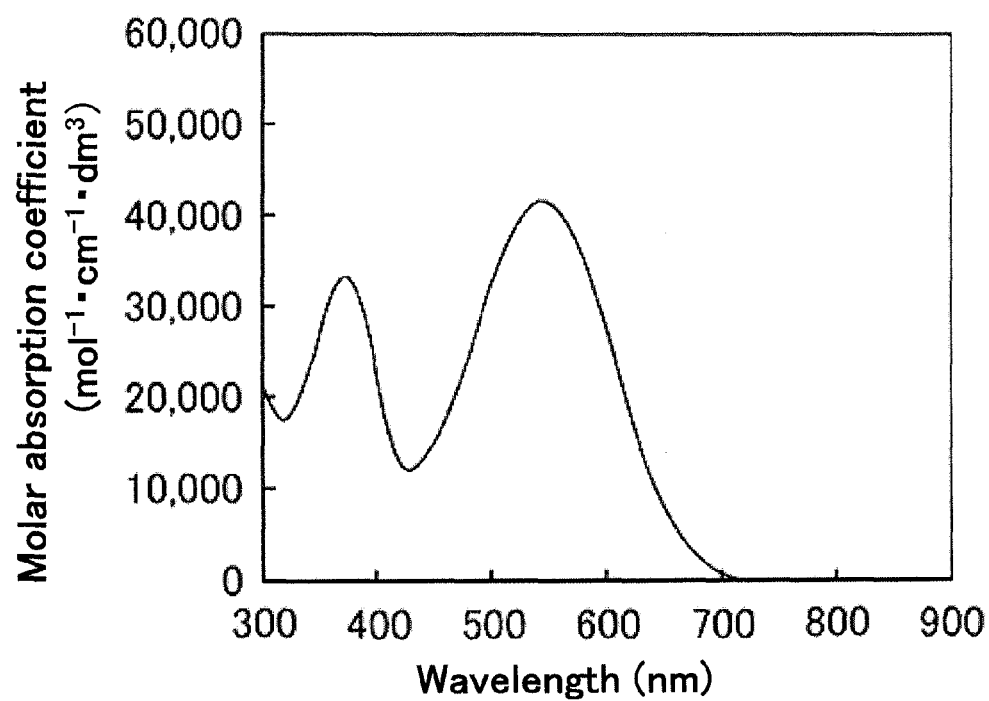
FIG. 3 is a chart showing the absorption spectrum of thiazole-based compound (TZ-2) disclosed in second exemplary embodiment.

In addition, the absorption spectrum of the obtained thiazole-based compound TZ-2 (dye) in THF is shown in FIG. 3. The $\lambda_{max}$ of this thiazole-based compound TZ-2 was 544 nm.

Third Exemplary Embodiment

Synthesis of Thiazole-Based Compound TZ-3

A thiazole-based compound TZ-3 was synthesized according to the following reaction scheme.

[Chemical formula 22]

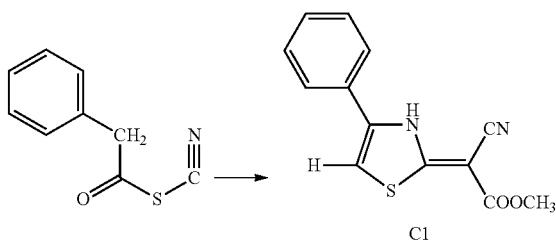

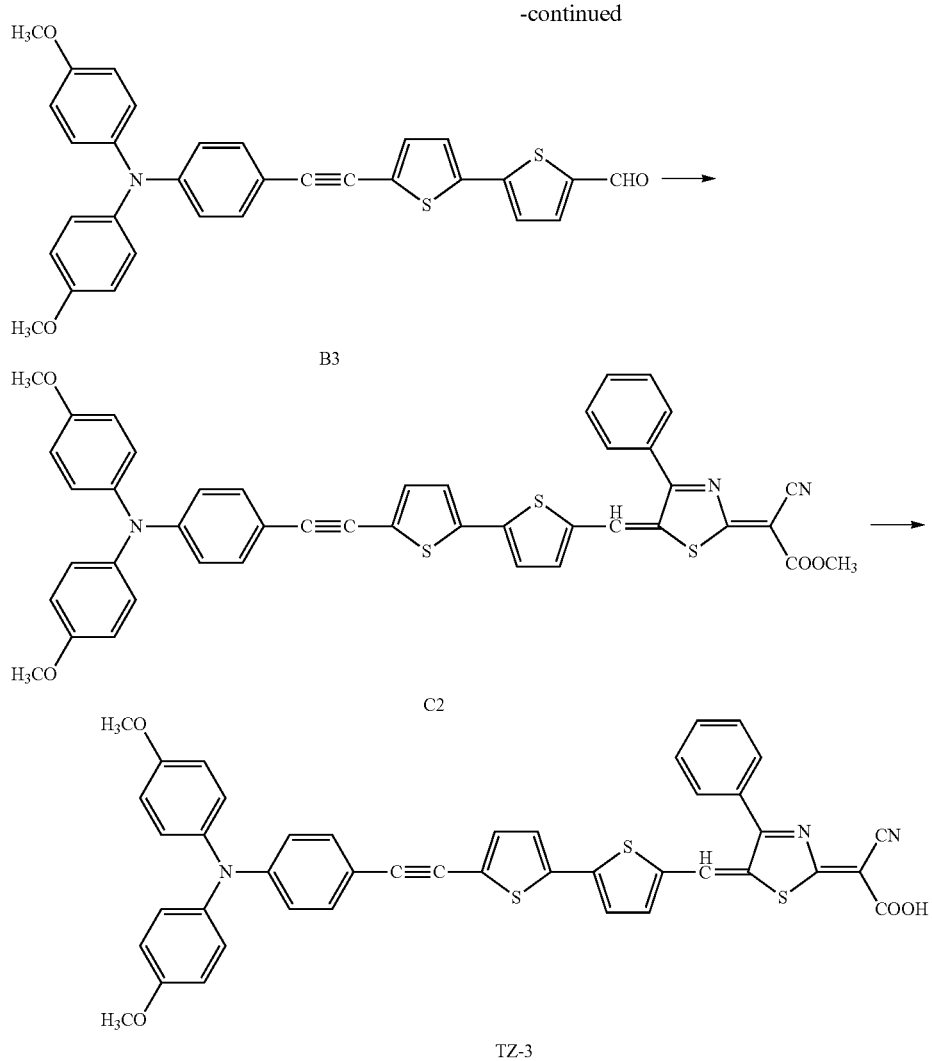

7 g of phenacyl thiocyanate and 3.91 g of methyl cyanoacetate were dissolved in 12 mL of DMF, and 12 mL of triethylamine was dropped thereinto. The mixture was stirred overnight at room temperature, and then, the reaction mixture was dropped into 500 mL of water comprising 20 mL of acetic acid. The precipitated crystals were filtered off, and washed with water and ethanol in this order to obtain 5.61 g of C1.

Next, 1.263 g of C1 and 1.5 g of B3 synthesized in the second exemplary embodiment were dissolved in 30 mL of chloroform, and 0.61 g of piperidine was added thereto. The mixture was heated to reflux for 8 hours. The mixture was allowed to cool, and then concentrated under reduced pressure. The residue was dissolved in 8 mL of THF, and the solution was dropped into 400 mL of water comprising 0.5 mL of concentrated hydrochloric acid. The precipitated crystals were filtered off, and washed with water and methanol in this order to obtain 0.174 g of C2.

Next, 0.16 g of C2 was dissolved in 15 mL of pyridine, and 0.28 g of lithium iodide was added thereto. The mixture was stirred at 115° C. for 6 hours. The mixture was allowed to cool, and then dropped into 400 mL of water, and the mixture was made acidic with dilute hydrochloric acid. The precipitated crystals were filtered off, water-washed, and dried. The obtained crystals were purified by a silica gel column (eluent: ethyl acetate) to obtain 0.04 g of the target thiazole-based compound TZ-3 (yield 25%).

Fourth Exemplary Embodiment

Fabrication of Photoelectric Conversion Device for Photoelectrochemical Cell

A photoelectric conversion device for a photoelectrochemical cell was fabricated as follows.

(a) Fabrication of Semiconductor Electrode for Photoelectrochemical Cell and Counter Electrode First, a semiconductor electrode for a photoelectrochemical cell was fabricated in the following order.

Glass with FTO (10 Ωcm²) with a size of 15 mm×15 mm and a thickness of 1.1 mm was prepared as a conductive substrate (a light-transmitting substrate with a transparent conductive layer).

In addition, a titanium oxide paste (the material of a semiconductor layer) was prepared as follows. 5 g of a commercially available titanium oxide powder (trade name: P25, manufactured by NIPPON AEROSIL CO., LTD., average primary particle diameter: 21 nm), 20 mL of a 15 vol % aqueous solution of acetic acid, 0.1 mL of a surfactant (trade name: Triton (registered trademark) X-100, manufactured by Sigma-Aldrich), and 0.3 g of polyethylene glycol (molecular weight 20000) (manufactured by Wako Pure Chemical Industries, Ltd., product code: 168-11285) were mixed, and this mixture was stirred by a stirring mixer for about 1 hour to obtain a titanium oxide paste.

Then, the titanium oxide paste was applied (application area: 10 mm×10 mm) to the glass with FTO by a "doctor blade" method so that the film thickness was about 50 μm. Then, the glass with FTO on which the titanium oxide paste was coated was placed in an electric furnace, fired in the air atmosphere at 450° C. for about 30 minutes, and naturally cooled to obtain a porous titanium oxide film on the glass with FTO.

Further, a light-scattering layer was formed on the titanium oxide film as follows. A paste of titanium oxide with an average particle diameter of 400 nm (trade name: PST-400C, manufactured by JGC Catalysts and Chemicals Ltd.) was applied to the above-described titanium oxide film to a thickness of 20 μm by a screen printing method, and then fired in the air atmosphere at 450° C. for about 30 minutes, and naturally cooled to obtain a light-scattering layer on the titanium oxide film. A semiconductor electrode before a dye was adsorbed was obtained as described above.

On the other hand, a counter electrode was fabricated as follows. A platinum layer with an average film thickness of 1 μm as a catalyst layer was vapor-deposited on a soda lime glass plate (thickness of 1.1 mm) by a vacuum deposition method to obtain a counter electrode.

(b) Adsorption of Dye

Next, a dye for photoelectric conversion was adsorbed on the above-described semiconductor layer composed of the titanium oxide film and the light-scattering layer. For the adsorption of the dye for photoelectric conversion, a solution in which the thiazole-based compound TZ-1 described in the first exemplary embodiment was dissolved in THF at a concentration of about $2\times10^{-4}$ mol/L was used. The above-described semiconductor electrode was dipped in this dye solution, and stored overnight. Then, the semiconductor electrode was taken out of the dye solution, rinsed with acetonitrile to remove the extra dye, and dried in air to obtain the semiconductor electrode on which the dye for photoelectric conversion was adsorbed.

(c) Cell Assembly

After the treatment for adsorption of the dye for photoelectric conversion, the above-described semiconductor electrode for a photoelectrochemical cell and the above-described counter electrode were disposed so that the semiconductor layer and the catalyst layer were opposed to each other, to form a cell with a gap that is ready to electrolyte injection. Next, a thermosetting resin film with a cut sufficient for an electrolyte to penetrate into the gap between the semiconductor electrode and the counter electrode was thermocompression-bonded to the outer peripheral portion of the cell.

(d) Injection of Electrolyte

An iodine-based electrolyte was injected into the above-described cell from the place where the above-described cut was made, and was allowed to penetrate into the gap between the semiconductor electrode and the counter electrode. For the iodine-based electrolyte, a solution using acetonitrile as a solvent with an iodine ($I_2$) concentration of 0.025 mol/L and a lithium iodide concentration of 2.0 mol/L was used.

(e) Measurement of Photocurrent

The photoelectric conversion device for a photoelectrochemical cell fabricated as described above was irradiated with light with an intensity of 100 mW/cm² under the condition of AM 1.5 by a solar simulator. The generated electricity was measured by a current-voltage measurement apparatus, and the photoelectric conversion performance was evaluated. As a result, the photoelectric conversion efficiency was 2.0%.

Fifth Exemplary Embodiment

A photoelectric conversion device was fabricated in similar manner to that disclosed in the fourth exemplary embodiment except that the thiazole-based compound TZ-2 was used instead of the thiazole-based compound TZ-1. As a result of evaluating the photoelectric conversion performance of the obtained photoelectric conversion device, a photoelectric conversion efficiency of 2.5% was obtained in the device using the thiazole-based compound TZ-2.

Sixth Exemplary Embodiment

A photoelectric conversion device was fabricated in similar manner to that disclosed in the fourth exemplary embodiment except that the thiazole-based compound TZ-3 was used instead of the thiazole-based compound TZ-1. As a result of evaluating the photoelectric conversion performance of the obtained photoelectric conversion device, a photoelectric conversion efficiency of 2.8% was obtained in the device using the thiazole-based compound TZ-3.

While the invention of the present application has been explained with reference to the embodiments (and the exemplary embodiments), the scope of the invention disclosed in the present application is not limited to the embodiments (and the exemplary embodiments) described above. Various modifications that may be understood by a person skilled in the art may be made in the constitutions and detailed features of the invention of the present application within the scope of the invention of the present application.

This application claims priority to Japanese Patent Application No. 2011-029218 filed on Feb. 14, 2011, the entire disclosure of which is incorporated herein.

INDUSTRIAL APPLICABILITY

As explained above, the thiazole-based compound, a tautomer or stereoisomer thereof, or a salt thereof according to the present invention is advantageously used as a sensitizing dye for a photoelectric conversion Such a dye for photoelectric conversion comprising the thiazole-based compound according to the present invention has excellent photoelectric conversion performance. In addition, precious metals, such as ruthenium, are not needed, and therefore, the problem of restriction in terms of resources is solved, and solar cells (for example, dye-sensitized solar cells) may be supplied more inexpensively. Therefore, solar cells (for example, dye-sensitized solar cells) may be applied for a wide range of uses. The uses of the thiazole-based compound according to the present invention are not limited to these, and the thiazole-based compound according to the present invention may be used in various fields.

Some or all of the embodiments described above may also be identified as the following notes, but the scope of the present invention is not limited to the modes stated in the following notes.

(Note 1)

A thiazole-based compound represented by the following general formula (1), a tautomer or stereoisomer thereof, or a salt thereof,

[Chemical formula 23]

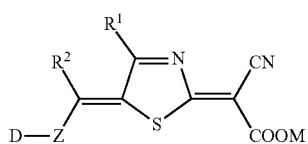
(1)

wherein $R^1$ represents a hydrogen atom, a substituted or unsubstituted, linear or branched alkyl group, or a substituted or unsubstituted aryl group, $R^2$ represents a hydrogen atom, a substituted or unsubstituted, linear or branched alkyl group, or a cyano group, D represents an organic group comprising an electron-donating substituent, Z represents a linking group having a heteroaromatic ring or at least one hydrocarbon group selected from the group consisting of an aromatic ring, a vinylene group (—CH═CH—), or an ethynylene group (—C≡C—), and M represents a hydrogen atom or a salt-forming cation.

(Note 2)

The thiazole-based compound, a tautomer or stereoisomer thereof, or a salt thereof according to note 1, wherein the organic group D comprising an electron-donating substituent is a group represented by the following general formula (2):

[Chemical formula 24]

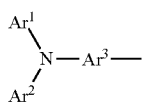
(2)

wherein $Ar^1$ and $Ar^2$ each independently represent a substituted or unsubstituted alkyl group, or a substituted or unsubstituted aryl group or heterocyclic group, and $Ar^3$ represents a substituted or unsubstituted arylene group, or a substituted or unsubstituted divalent heterocyclic group.

As the substituted or unsubstituted divalent heterocyclic group used for $Ar^3$, a substituted or unsubstituted divalent heteroaromatic ring group may be preferably used. In addition, as the substituted or unsubstituted heterocyclic group used for $Ar^1$ and $Ar^2$, a substituted or unsubstituted heteroaromatic ring group may be preferably used.

(Note 3)

The thiazole-based compound, a tautomer or stereoisomer thereof, or a salt thereof according to note 1, wherein the organic group D comprising an electron-donating substituent is a group represented by the following general formula (3):

[Chemical formula 25]

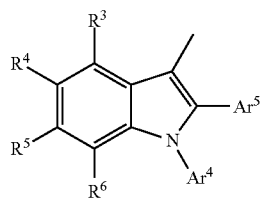
(3)

wherein $Ar^4$ and $Ar^5$ each independently represent a substituted or unsubstituted alkyl group, or a substituted or unsubstituted aryl group or heteroaromatic ring group, and $R^3$ to $R^6$ each independently represent a hydrogen atom, a substituted or unsubstituted, linear or branched alkyl group, a substituted or unsubstituted aryl group, an alkoxy group, a hydroxyl group, or a N,N-dialkylamino group.

(Note 4)

The thiazole-based compound, a tautomer or stereoisomer thereof, or a salt thereof according to note 1, wherein the organic group D comprising an electron-donating substituent is a group represented by any one of the following formulae (D1) to (D13):

[Chemical formula 26]

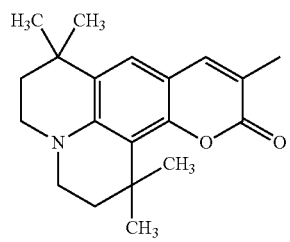
(D1)

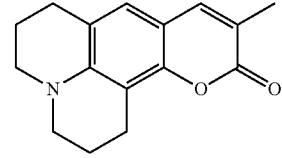
(D2)

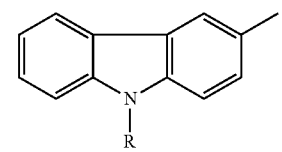
(D3)

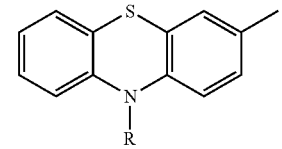
(D4)

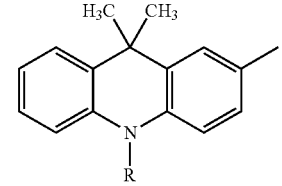
(D5)

-continued (D6) 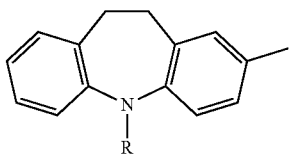

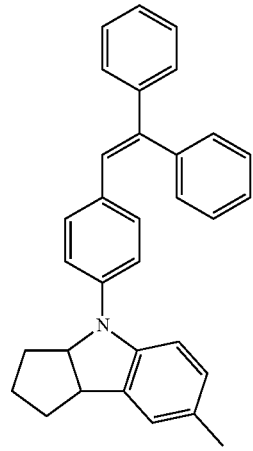

[Chemical formula 27]

(D7)

(D8)

(D9)

(D10) 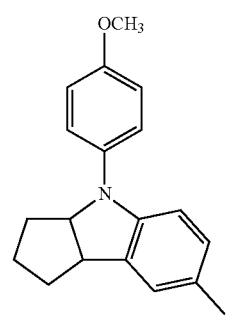

(D11) 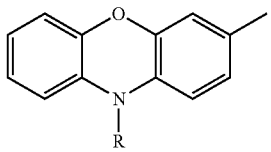

(D12) 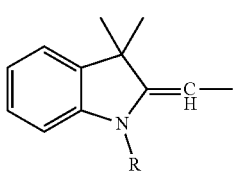

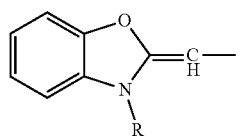

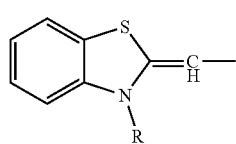

-continued (D13) 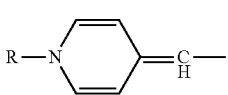

wherein R in the formulae (D3) to (D6) and (D9) to (D13) represents a substituted or unsubstituted alkyl group, or a substituted or unsubstituted aryl group.

(Note 5)

The thiazole-based compound, a tautomer or stereoisomer thereof, or a salt thereof according to any one of note 1 to note 4, wherein the linking group Z is a moiety comprising a structure represented by the following general formula (4):

[Chemical formula 28]

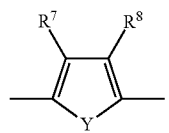 (4)

wherein $R^7$ and $R^8$ each independently represent a hydrogen atom, a substituted or unsubstituted, linear or branched alkyl group, or a substituted or unsubstituted, linear or branched alkoxy group, $R^7$ and $R^8$ may be linked to each other to form a ring, Y represents an oxygen atom, a sulfur atom, or NRa, and Ra represents a hydrogen atom, a substituted or unsubstituted, linear or branched alkyl group, or a substituted or unsubstituted aryl group.

(Note 6)

The thiazole-based compound, a tautomer or stereoisomer thereof, or a salt thereof according to note 5, wherein, in $R^7$ and $R^8$, the number of carbon atoms of the alkyl group is selected from 1 to 12, and the number of carbon atoms of the aryl group is selected from 5 to 24.

(Note 7)

The thiazole-based compound, a tautomer or stereoisomer thereof, or a salt thereof according to any one of note 1 to note 4, wherein Z is represented by any one of the following formulae (Z1) to (Z29):

[Chemical formula 29]

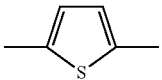 (Z1)

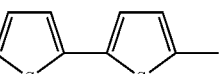 (Z2)

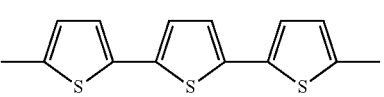 (Z3)

-continued
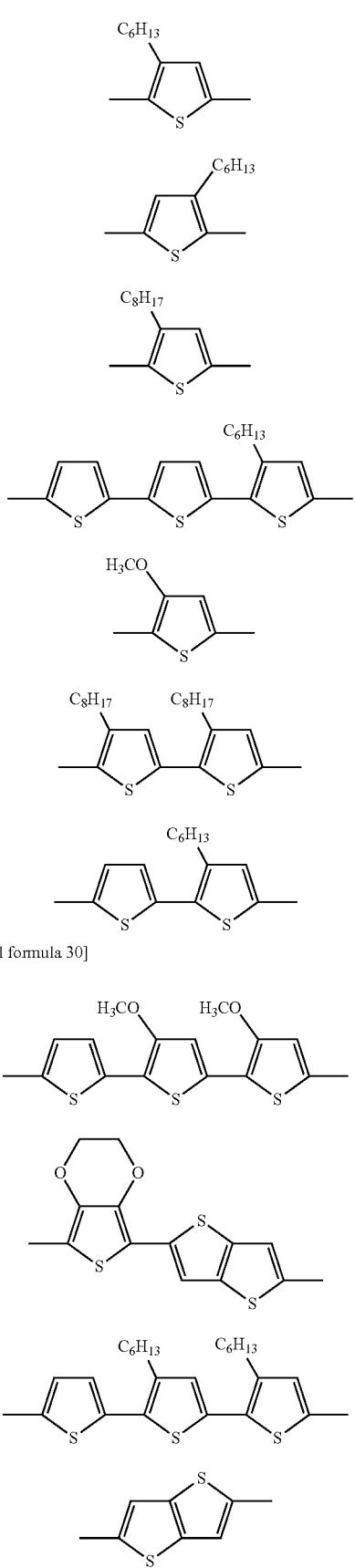
[Chemical formula 30]
-continued
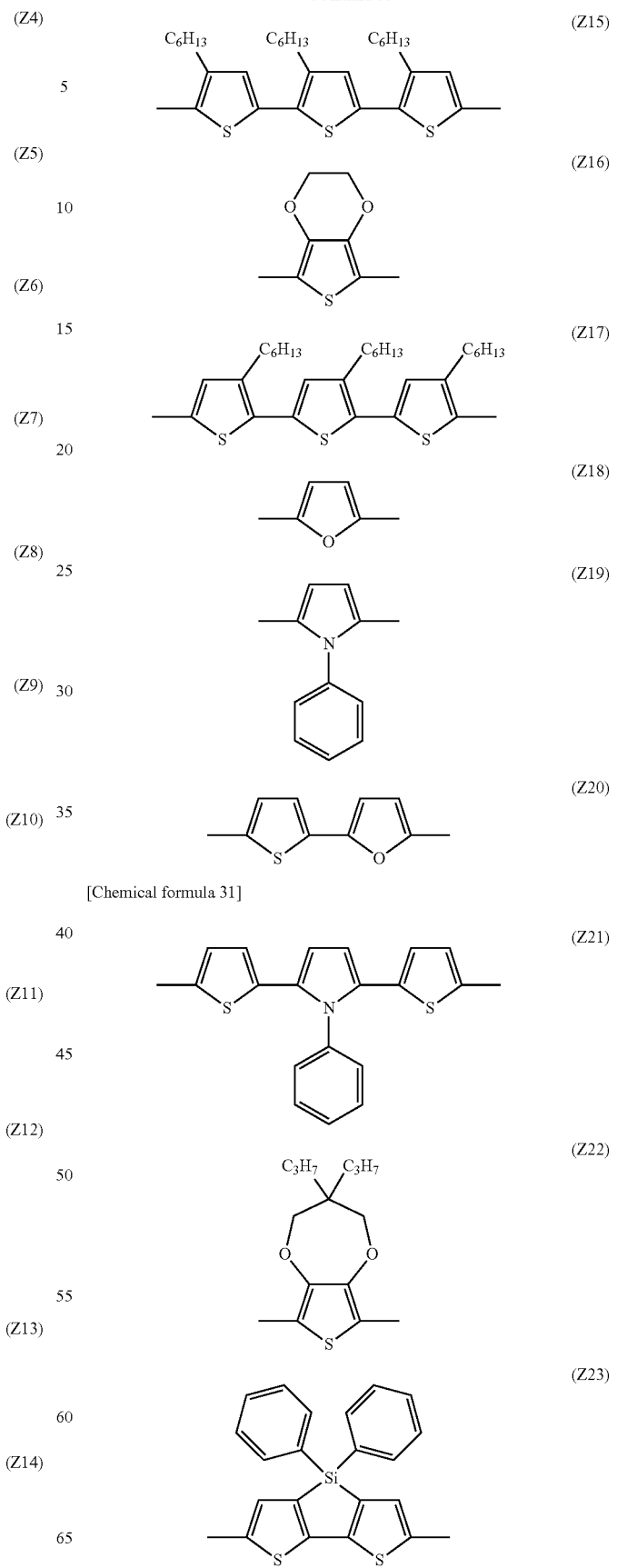
[Chemical formula 31]

-continued (Z24) 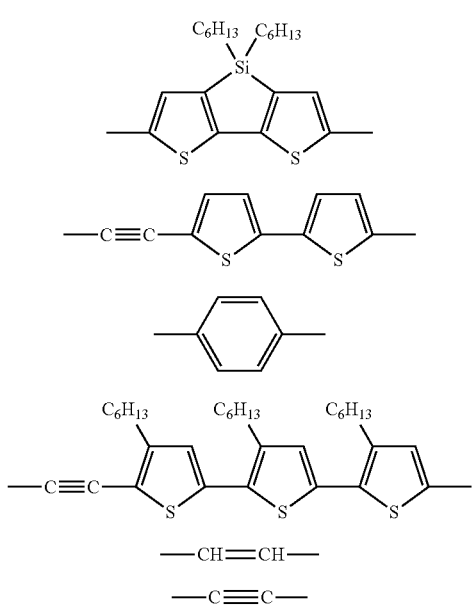

(Z25)

(Z26)

(Z27)

(Z28) —CH=CH—

(Z29) —C≡C—

(Note 8)

The thiazole-based compound, a tautomer or stereoisomer thereof, or a salt thereof according to note 1,
represented by the following formula TZ-1:

[Chemical formula 32]

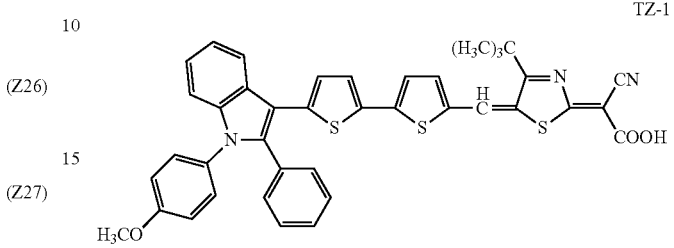

TZ-1

(Note 9)

The thiazole-based compound, a tautomer or stereoisomer thereof, or a salt thereof according to note 1,
represented by the following formula TZ-2:

[Chemical formula 33]

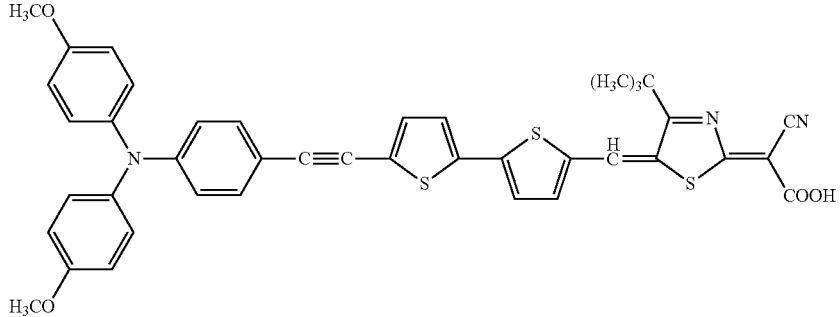

TZ-2

(Note 10)

The thiazole-based compound, a tautomer or stereoisomer thereof, or a salt thereof according to note 1,
represented by the following formula TZ-3:

[Chemical formula 34]

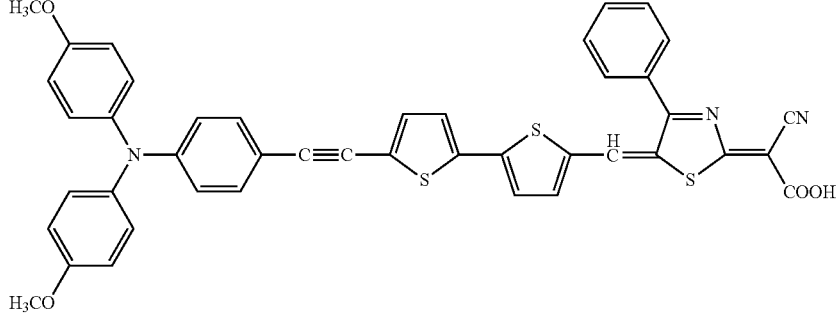

TZ-3

(Note 11)
A dye for photoelectric conversion,
comprising at least one of the thiazole-based compound, a tautomer or stereoisomer thereof, or a salt thereof according to any one of note 1 to note 10.
(Note 12)
A semiconductor electrode for a photoelectrochemical cell,
comprising a semiconductor layer comprising the dye for photoelectric conversion according to note 11.
(Note 13)
The semiconductor electrode for a photoelectrochemical cell according to note 12,
wherein the semiconductor layer is at least one selected from the group consisting of a single-element semiconductor, a compound semiconductor, a metal chalcogenide, and a semiconductive compound having a perovskite structure.
(Note 14)
The semiconductor electrode for a photoelectrochemical cell according to note 13,
wherein the single-element semiconductor is at least one of silicon and germanium.
(Note 15)
The semiconductor electrode for a photoelectrochemical cell according to note 13 or note 14,
wherein the metal chalcogenide is at least one selected from the group consisting of an oxide of titanium, tin, zinc, iron, tungsten, indium, zirconium, vanadium, niobium, tantalum, strontium, hafnium, cerium, or lanthanum; a sulfide of cadmium, zinc, lead, silver, antimony, or bismuth; a selenide of cadmium or lead; and a telluride of cadmium.
(Note 16)
The semiconductor electrode for a photoelectrochemical cell according to any one of note 13 to note 15,
wherein the compound semiconductor is at least one selected from the group consisting of the metal chalcogenide stated in note 15; a phosphide of zinc, gallium, indium, or cadmium; gallium arsenide; copper-indium-selenide; and copper-indium-sulfide.
(Note 17)
The semiconductor electrode for a photoelectrochemical cell according to any one of note 13 to note 16,
wherein the semiconductor compound having a perovskite structure is at least one selected from the group consisting of barium titanate, strontium titanate, and potassium niobate.
(Note 18)
The semiconductor electrode for a photoelectrochemical cell according to any one of note 12 to note 17,
wherein the semiconductor layer comprises titanium oxide or zinc oxide.
(Note 19)
A photoelectric conversion device for a photoelectrochemical cell,
comprising the semiconductor electrode for a photoelectrochemical cell according to any one of note 12 to note 18.
(Note 20)
The photoelectric conversion device for a photoelectrochemical cell according to note 19,
further comprising a counter electrode opposed to the semiconductor electrode for a photoelectrochemical cell, and
comprising a charge transporting material between the counter electrode and the semiconductor electrode for a photoelectrochemical cell.
(Note 21)
A photoelectrochemical cell,
comprising the photoelectric conversion device for a photoelectrochemical cell according to note 19 or note 20.

(Note 22)
A method for producing the thiazole-based compound, a tautomer or stereoisomer thereof, or a salt thereof according to any one of note 1 to note 10, comprising:
a condensation step of producing a compound represented by the following general formula (III) by a condensation reaction of a compound represented by the following general formula (I) and a compound represented by the following general formula (II); and
a hydrolysis (deprotection) step of hydrolyzing (deprotecting) the compound represented by the following general formula (III) to produce a thiazole-based compound represented by the general formula (1),

[Chemical formula 35]

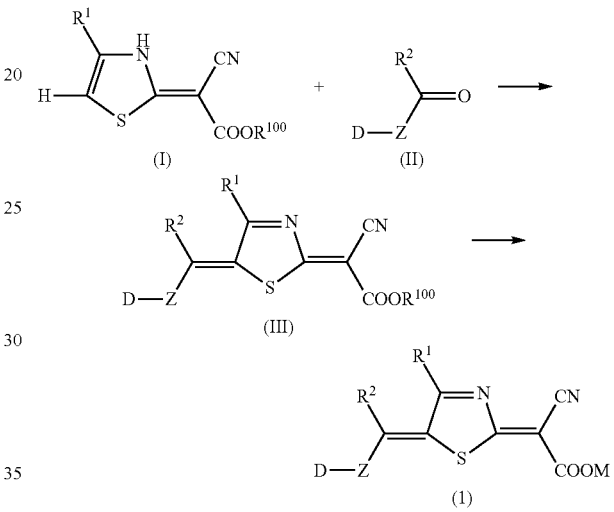

wherein, in the general formula (I) and general formula (III),
$R^1$ is the same as $R^1$ defined in the general formula (1), and
$R^{100}$ is a protecting group, and
in the general formula (II) and general formula (III),
$R^2$, D, and Z are the same as $R^2$, D, and Z, respectively, defined in the general formula (1).
(Note 23)
The production method according to note 22,
wherein, in the general formula (I) and general formula (III),
$R^{100}$ is a hydrocarbon group, and may be linear, branched, or cyclic, may be saturated or unsaturated, and may or may not have a substituent.
(Note 24)
The production method according to note 22,
wherein, in the general formula (I) and general formula (III),
$R^{100}$ is a substituted or unsubstituted alkyl group.
(Note 25)
The production method according to any one of note 22 to note 24,
further comprising a ring-closing step of ring-synthesizing from a compound represented by the following general formula (IV) and a compound represented by the following general formula (V) to produce a compound represented by the general formula (I),

[Chemical formula 36]

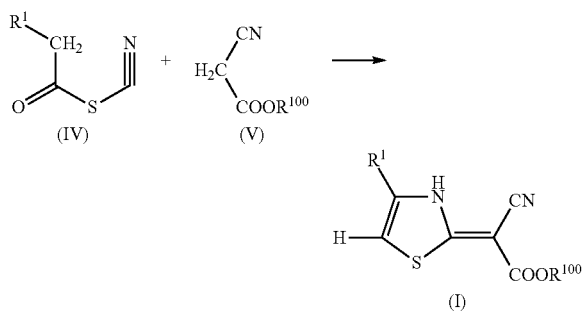

wherein, in the general formula (IV), $R^1$ is the same as $R^1$ defined in the general formula (I), and
in the general formula (V), $R^{100}$ is the same as $R^{100}$ defined in the general formula (I).
(Note 26)
The production method according to any one of note 22 to note 25,
further comprising a thiocyanidation step of reacting a compound represented by the following general formula (VI) with a thiocyanate to produce a compound represented by the general formula (IV),

[Chemical formula 37]

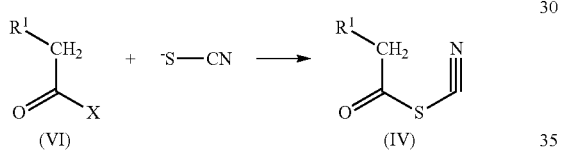

wherein, in the general formula (VI), $R^1$ is the same as $R^1$ defined in the general formula (IV), and in the general formula (VI), X is a halogen atom, for example, Cl, Br, or I.

The invention claimed is:

1. A thiazole-based compound represented by the following general formula (1), a tautomer or stereoisomer thereof, or a salt thereof,

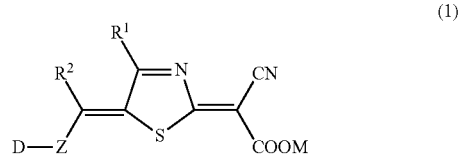

wherein
$R^1$ represents hydrogen atom, a substituted or unsubstituted, linear or branched alkyl group, or a substituted or unsubstituted aryl group,
$R^2$ represents a hydrogen atom, a substituted or unsubstituted, linear or branched alkyl group, or a cyano group,
D represents an organic group comprising an electron-donating substituent,
Z represents a linking group having a heteroaromatic ring or at least one hydrocarbon group selected from the group consisting of an aromatic ring, a vinylene group (—CH═CH—), or an ethynylene group (—C≡C—), and
M represents hydrogen atom or a salt-forming cation.

2. The thiazole-based compound, a tautomer or stereoisomer thereof, or a salt thereof according to claim 1,
wherein the organic group D comprising an electron-donating substituent is a group represented by the following general formula (2):

wherein
$Ar^1$ and $Ar^2$ each independently represents a substituted or unsubstituted alkyl group, a substituted or unsubstituted aryl group, or a substituted or unsubstituted heterocyclic group, and
$Ar^3$ represents a substituted or unsubstituted arylene group, or a substituted or unsubstituted divalent heterocyclic group.

3. The thiazole-based compound, a tautomer or stereoisomer thereof, or a salt thereof according to claim 2,
wherein the linking group Z is a moiety comprising a structure represented by the following general formula (4):

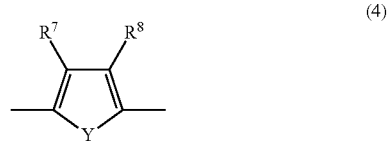

wherein
$R^7$ and $R^8$ each independently represents a hydrogen atom, a substituted or unsubstituted, linear or branched alkyl group, or a substituted or unsubstituted, linear or branched alkoxy group,
$R^7$ and $R^8$ may be linked to each other to form a ring,
Y represents an oxygen atom, a sulfur atom, or NRa, and
Ra represents a hydrogen atom, a substituted or unsubstituted, linear or branched alkyl group, or a substituted or unsubstituted aryl group.

4. A dye for photoelectric conversion,
comprising at least one of a thiazole-based compound, a tautomer or stereoisomer thereof, or a salt thereof according to claim 2.

5. The thiazole-based compound, a tautomer or stereoisomer thereof, or a salt thereof according to claim 1,
wherein the organic group D comprising an electron-donating substituent is a group represented by the following general formula (3):

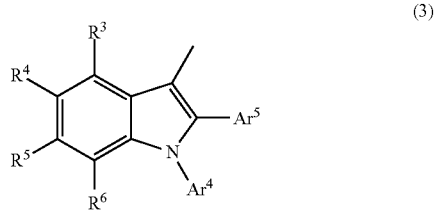

wherein
Ar⁴ and Ar⁵ each independently represents a substituted or unsubstituted alkyl group, a substituted or unsubstituted aryl group, or a substituted or unsubstituted heteroaromatic ring group, and R³ to R⁶ each independently represents a hydrogen atom, a substituted or unsubstituted, linear or branched alkyl group, a substituted or unsubstituted aryl group, an alkoxy group, a hydroxyl group, or a N,N-dialkylamino group.

6. The thiazole-based compound, a tautomer or stereoisomer thereof, or a salt thereof according to claim 5,
wherein the linking group Z is a moiety comprising a structure represented by the following general formula (4):

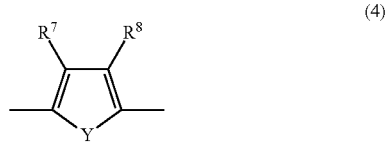

(4)

wherein
R⁷ and R⁸ each independently represents a hydrogen atom, a substituted or unsubstituted, linear or branched alkyl group, or a substituted or unsubstituted, linear or branched alkoxy group, R⁷ and R⁸ may be linked to each other to form a ring, Y represents an oxygen atom, a sulfur atom, or NRa, and Ra represents a hydrogen atom, a substituted or unsubstituted, linear or branched alkyl group, or a substituted or unsubstituted aryl group.

7. A dye for photoelectric conversion,
comprising at least one of a thiazole-based compound, a tautomer or stereoisomer thereof, or a salt thereof according to claim 5.

8. The thiazole-based compound, a tautomer or stereoisomer thereof, or a salt thereof according to claim 1,
wherein the linking group Z is a moiety comprising a structure represented by the following general formula (4):

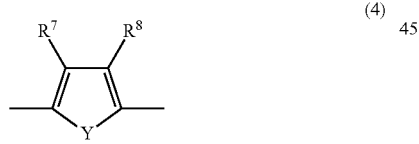

(4)

wherein
R⁷ and R⁸ each independently represents a hydrogen atom, a substituted or unsubstituted, linear or branched alkyl group, or a substituted or unsubstituted, linear or branched alkoxy group, R⁷ and R⁸ may be linked to each other to form a ring, Y represents an oxygen atom, a sulfur atom, or NRa, and Ra represents a hydrogen atom, a substituted or unsubstituted, linear or branched alkyl group, or a substituted or unsubstituted aryl group.

9. A dye for photoelectric conversion,
comprising at least one of a thiazole-based compound, a tautomer or stereoisomer thereof, or a salt thereof according to claim 8.

10. A dye for photoelectric conversion,
comprising at least one of a thiazole-based compound, a tautomer or stereoisomer thereof, or a salt thereof according to claim 1.

11. A semiconductor electrode for a photoelectrochemical cell,
comprising a semiconductor layer comprising a dye for photoelectric conversion according to claim 10.

12. The semiconductor electrode for a photoelectrochemical cell according to claim 11,
wherein the semiconductor layer comprises titanium oxide or zinc oxide.

13. A photoelectric conversion device for a photoelectrochemical cell,
comprising a semiconductor electrode for a photoelectrochemical cell according to claim 12.

14. The photoelectric conversion device for a photoelectrochemical cell according to claim 13,
further comprising a counter electrode opposed to the semiconductor electrode for a photoelectrochemical cell, and a charge transporting material between the semiconductor electrode for a photoelectrochemical cell and the counter electrode.

15. A photoelectrochemical cell comprising a photoelectric conversion device for a photoelectrochemical cell according to claim 14.

16. A photoelectric conversion device for a photoelectrochemical cell,
comprising a semiconductor electrode for a photoelectrochemical cell according to claim 11.

17. The photoelectric conversion device for a photoelectrochemical cell according to claim 16,
further comprising a counter electrode opposed to the semiconductor electrode for a photoelectrochemical cell, and a charge transporting material between the semiconductor electrode for a photoelectrochemical cell and the counter electrode.

18. A photoelectrochemical cell comprising a photoelectric conversion device for a photoelectrochemical cell according to claim 17.

19. A photoelectrochemical cell comprising a photoelectric conversion device for a photoelectrochemical cell according to claim 16.

* * * * *